(12) United States Patent
Yonetoku et al.

(10) Patent No.: US 7,947,690 B2
(45) Date of Patent: May 24, 2011

(54) PYRIMIDINE DERIVATIVE CONDENSED WITH A NON-AROMATIC RING

(75) Inventors: Yasuhiro Yonetoku, Tokyo (JP); Kenji Negoro, Tokyo (JP); Kenichi Onda, Tokyo (JP); Masahiko Hayakawa, Tokyo (JP); Daisuke Sasuga, Tokyo (JP); Takahiro Nigawara, Tokyo (JP); Kazuhiko Iikubo, Tokyo (JP); Hiroyuki Moritomo, Tokyo (JP); Shigeru Yoshida, Tokyo (JP); Takahide Ohishi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 851 days.

(21) Appl. No.: 11/577,648

(22) PCT Filed: Oct. 17, 2005

(86) PCT No.: PCT/JP2005/019000
§ 371 (c)(1),
(2), (4) Date: Apr. 20, 2007

(87) PCT Pub. No.: WO2006/043490
PCT Pub. Date: Apr. 27, 2006

(65) Prior Publication Data
US 2008/0070896 A1 Mar. 20, 2008

(30) Foreign Application Priority Data
Oct. 20, 2004 (JP) ................................. 2004-305374

(51) Int. Cl.
*A61K 31/519* (2006.01)
*A61K 31/497* (2006.01)
*C07D 495/04* (2006.01)
*A61P 3/10* (2006.01)
*C07D 487/04* (2006.01)
*C07D 471/04* (2006.01)
*C07D 239/72* (2006.01)
*A61K 31/517* (2006.01)

(52) U.S. Cl. ..................... 514/260.1; 544/278; 544/280; 544/279; 544/253; 514/252.16; 514/264.1; 514/265.1; 514/266.1; 514/266.22; 514/258.1

(58) Field of Classification Search .................. 544/278; 514/260.1
See application file for complete search history.

(56) References Cited

U.S. PATENT DOCUMENTS

| | | | |
|---|---|---|---|
| 3,272,811 A | 9/1966 | Ohnacker et al. | |
| 4,871,739 A | 10/1989 | Baldwin et al. | |
| 4,889,856 A * | 12/1989 | Tolman et al. | 514/252.16 |
| 6,627,628 B1 | 9/2003 | Schindler et al. | |
| 6,660,746 B1 | 12/2003 | Schindler et al. | |
| 2003/0199526 A1 | 10/2003 | Choquette et al. | |
| 2005/0004143 A1 | 1/2005 | Dugar et al. | |
| 2005/0187217 A1 | 8/2005 | Wilson et al. | |
| 2006/0229306 A1 | 10/2006 | Terricabras Belart et al. | |

FOREIGN PATENT DOCUMENTS

| | | |
|---|---|---|
| EP | 0 276 057 A2 | 7/1988 |
| JP | 4-224580 | 8/1992 |
| JP | 2004-509115 | 3/2004 |
| WO | WO 00/31047 | 6/2000 |
| WO | WO 00/46214 | 8/2000 |
| WO | WO 02/22605 A1 | 3/2002 |
| WO | WO 03/049739 A1 | 6/2003 |
| WO | WO 2004/065391 A1 | 8/2004 |
| WO | WO 2004/087056 A2 | 10/2004 |
| WO | WO 2005/014558 A1 | 2/2005 |

OTHER PUBLICATIONS

"The Effect of Intensive Treatment of Diabetes on the Development and Progression of Long-Term Complications in Insulin-Dependent Diabetes Mellitus", The New England Journal of Medicine, vol. 329, No. 14, Sep. 30, 1993, pp. 977-986.

"Glucose Tolerance and Mortality: Comparison of Who and American Diabetic Association Diagnostic Criteria", The Lancet, vol. 354, 1999, pp. 617-621.

Irene M. Stratton, et al. "Association of Glycaemia With Macrovascular and Microvascular Complications of Type 2 Diabetes (UKPDS 35): Prospective Observational Study", British Medical Journal, vol. 321, Aug. 12, 2000, pp. 405-413.

Augusto C. Tome, et al. "New Pyrimidine and Pyrimidone Derivatives of [60] Fullerene", Tetrahedron, vol. 54, 1998, pp. 11141-11150.

Augusto C. Tome, et al. "Pyrimidine and Pyrimidone Derivatives of [60] Fullerene", Tetrahedron Letters, vol. 38, No. 14, 1997, pp. 2557-2560.

Sachio Ohno, et al., "Synthesis and Hypoglycemic Activity of 7,8-Dihydro-6H-thiopyrano[3,2-d]pyrimidine Derivatives and Related Compounds", Chemical and Pharmaceutical Bulletin, Pharmaceutical Society of Japan, vol. 34, No. 10, XP000196068, Oct. 1, 1986, pp. 4150-4165.

* cited by examiner

*Primary Examiner* — Susanna Moore
(74) *Attorney, Agent, or Firm* — Oblon, Spivak, McClelland, Maier & Neustadt, L.L.P.

(57) ABSTRACT

The present invention provides a condensed pyrimidine compound represented by formula (I) or pharmaceutically acceptable salt thereof:

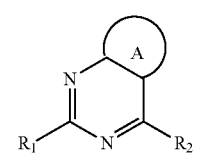

(I)

where A represents a ring

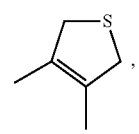

where at least one carbon atom within said ring is optionally substituted with one or more groups selected from the group consisting of lower alkyl, —O-(lower alkyl), halogen atom, carboxyl, —CO$_2$-(lower alkyl), and carbamoyl, $R^1$ represents: (1) phenyl substituted with at least three halogen atoms, which may have at least one additional substituent, or (2) cyclopropyl, cyclobutyl, cyclopentyl, cyclohexyl, or cycloheptyl, each of which is optionally substituted; and $R^2$ represents a group represented by formula (II) or an optionally substituted cyclic amino:

wherein $R^{21}$ and $R^{22}$ may be identical or different and each represents —H, lower alkyl, lower alkenyl, lower alkynyl, cycloalkyl, phenyl, heteroaryl, non-aromatic heterocyclyl, or —O-(lower alkyl), each of which is optionally substituted.

13 Claims, No Drawings

PYRIMIDINE DERIVATIVE CONDENSED WITH A NON-AROMATIC RING

TECHNICAL FIELD

The present invention relates to new pyrimidine derivatives condensed with a non-aromatic ring or pharmaceutically acceptable salts thereof useful as drugs, particularly as insulin secretagogues or diabetic therapeutic agents, and a drug comprising these compounds as active ingredients.

BACKGROUND ART

Diabetes is a disease with chronic hyperglycemia as a cardinal sign and develops by absolute or relative deficiency of insulin activity. Clinically, diabetes is roughly classified by the characteristics into insulin-dependent diabetes (referred to as "type 1 diabetes" hereinafter) and non-insulin-dependent diabetes (referred to as "type 2 diabetes" hereinafter). In type 2 diabetes, which accounts for approximately 90% of diabetic patients, decrease of insulin secretion from the pancreatic β-cells is one of major causes of the onset, and postprandial hyperglycemia caused by early disorder in insulin secretion is particularly recognized. Presently, sulfonylurea drug (SU drug) is the mainstream as the insulin secretagogue, but it is likely to cause hypoglycemia and known to cause secondary ineffectiveness due to pancreatic exhaustion following long-term administration. Moreover, SU drug is effective to control blood glucose between meals, but has difficulty in suppressing postprandial hyperglycemia. Recent large-scale clinical trials have confirmed that remedying postprandial hyperglycemia is critical in controlling diabetic complications and diabetic development (Non-Patent Document 1). It is also reported that arteriosclerosis develops only during periods of the postprandial hyperglycemia and that the persistence of minor postprandial hyperglycemia increases mortality caused by cardiovascular disease or the like (Non-Patent Documents 2 and 3). This indicates that postprandial hyperglycemia is, even at minor levels, an independent risk factor of cardiovascular death. From the above background, attention has been paid to importance and necessity for medications against postprandial hyperglycemia. Hence, drugs having promoting activity on insulin secretion are considered to have an appropriate profile to remedy postprandial hyperglycemia and/or fasting blood glucose and to be useful for treating and preventing type 1 and type 2 diabetes.

WO 00/31047 pamphlet (Patent Document 1) discloses cyclopentane-condensed pyrimidine derivatives as compounds with activity to increase cyclic guanosine monophosphate (cGMP) level by activation of soluble guanylate cyclase, and diabetes is included in examples of diseases or morbidity in which increase in cGMP level is desired or said compounds can be used for therapy and prevention thereof. However, the document gives neither specific disclosure of the compounds of the present invention nor specific data indicating their applicability to diabetes therapy such as promoting activity on insulin secretion.

WO 00/46214 pamphlet (Patent Document 2) discloses cyclohexane-condensed pyrimidine derivatives as compounds with activity to increase cyclic guanosine monophosphate (cGMP) level by activation of soluble guanylate cyclase, and diabetes is included in examples of diseases or morbidity in which increase in cGMP level is desired or said compounds can be used for therapy and prevention thereof. However, the document gives neither specific disclosure of the compounds of the present invention nor specific data indicating their applicability to diabetes therapy such as promoting activity on insulin secretion.

WO 03/049739 pamphlet (Patent Document 3) discloses condensed pyrimidine derivatives as glycogen synthase kinase-3 (GSK-3) inhibitors and describes diabetes as an example of diseases for which these compounds are useful, that is, diseases caused by action of GSK-3. However, none of compounds of the present invention are specifically disclosed therein, and there are not disclosed specific data indicating applicability of said compounds to diabetes therapy such as promoting activity on insulin secretion, either.

WO 2004/065391 pamphlet (Patent Document 4) discloses thiophene-condensed pyrimidine derivatives substituted with a cyano group as phosphodiesterase 7 (PDE 7) inhibitors and describes type 1 and type 2 diabetes as examples of diseases that are expected to be improved by inhibition of PDE 7. However, neither compounds of the present invention are specifically disclosed, nor are specific data indicating their applicability to diabetes therapy such as promoting activity on insulin secretion.

Japanese Patent Laid-Open Publication H4-224580 (Patent Document 5) discloses nitrogen-containing ring-condensed pyrimidine derivatives as compounds with bactericidal activity, but does not specifically disclose the compounds of the present invention. Neither description nor suggestion is given on applicability of said compounds to diabetes therapy including promotion of insulin secretion, either.

WO 2004/087056 pamphlet (Patent Document 6) discloses condensed pyrimidine derivatives as transforming growth factor-beta (TGF-β) inhibitors, but does not specifically disclose the compounds of the present invention. The document gives neither description nor suggestion on applicability of said compounds to diabetes therapy including promotion of insulin secretion, either.

EP 0 276 057 (Patent Document 7) discloses pyrimidine derivatives condensed with a sulfur-containing ring as β-adrenaline blockers, but the document neither specifically discloses the compounds of the present invention nor gives description or suggestion on applicability of said compounds to diabetes therapy including promotion of insulin secretion.

WO 2005/014558 (Patent Document 8) discloses condensed pyrimidine derivatives as ion channel inhibitors, but does not specifically disclose the compounds of the present invention. It neither describes nor suggests that applicability of said compounds to diabetes therapy including promotion of insulin secretion.

Pyrimidine derivatives condensed with a sulfur-containing ring are also known as intermediates in synthesis of $C_{60}$ derivatives (Non-Patent Documents 4 and 5).

Non-Patent Document 1: N. Engl. J. Med., 329, 977-986, 1993
Non-Patent Document 2: Lancet, 354, 617, 1999
Non-Patent Document 3: Brit. Med. J., 321, 405-413, 2000
Non-Patent Document 4: Tetrahedron, 54(37), 11141-11150, 1998
Non-Patent Document 5: Tetrahedron Letters, 38(14), 2557-2560, 1997
Patent Document 1: WO 00/31047
Patent Document 2: WO 00/46214
Patent Document 3: WO 03/049739
Patent Document 4: WO 2004/065391
Patent Document 5: Japanese Patent Laid-Open Publication H4-224580
Patent Document 6: WO 2004/087056
Patent Document 7: EP 0 276 057
Patent Document 8: WO 2005/014558

DISCLOSURE OF THE INVENTION

Problems to be Solved by the Invention

As described above, since insulin secretagogues are useful for treating and preventing type 1 diabetes, type 2 diabetes, and insulin-resistant diseases, creation of further superior insulin secretagogues is earnestly desired.

Means for Solving the Problems

The present inventors earnestly studied compounds with promoting activity on insulin secretion, found that the pyrimidine derivatives condensed with a non-aromatic ring of the present invention have excellent effects of promoting insulin secretion, and completed the present invention.

That is, the present invention provides condensed pyrimidine derivatives represented by formula (I) or pharmaceutically acceptable salts thereof, a pharmaceutical composition containing these compounds as active ingredients, and a pharmaceutical composition serving as a therapeutic agent for type 1 diabetes, type 2 diabetes, and/or insulin-resistant diseases.

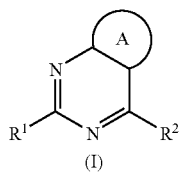
[Formula 1]
(I)

[Symbols in the formula represent the following meaning.
A:
A ring selected from the group consisting of Group $X^1$, Group $X^2$, Group $X^3$, and Group $X^4$. The carbon atoms composing this ring are optionally substituted with one or more substituents selected from the group consisting of lower alkyl, —O-(lower alkyl), halogen atom, carboxyl, —$CO_2$-(lower alkyl), and carbamoyl. The sulfur atom composing this ring may be oxidized.
Group $X^1$: A group consisting of

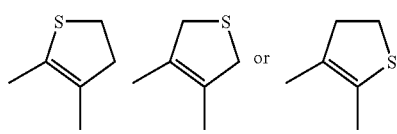
[Formula 2]

Group $X^2$: A group consisting of

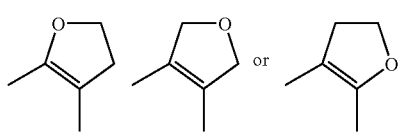
[Formula 3]

Group $X^3$: A group consisting of

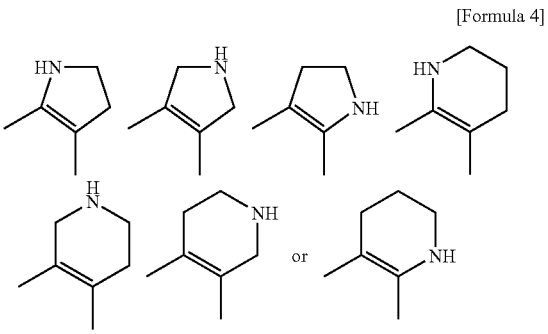
[Formula 4]

Group $X^4$: A group consisting of

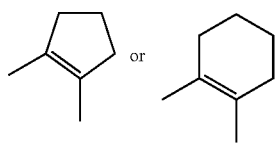
[Formula 5]

-$R^1$:
A group selected from Groups (1) to (3) below
(1) phenyl substituted with at least one halogen atom, which may have (an) additional substituent(s)
(2) cyclopropyl, cyclobutyl, cyclopentyl, cyclohexyl, or cycloheptyl, each of which is optionally substituted
(3) pyridyl, pyridazinyl, pyrimidinyl, pyrazinyl, pyrrolyl, thienyl, thiazolyl, oxazolyl, imidazolyl, isothiazolyl, isoxazolyl, pyrazolyl, or furyl substituted with at least one halogen atom. These rings are optionally substituted with one or more identical or different halogen atoms. These rings bond to the 2-position of the pyrimidine ring in formula (I) via a carbon atom composing said rings.
However, when A is a ring selected from Group $X^4$, —$R^1$ represents phenyl substituted with at least three halogen atoms.
—$R^2$:
A group represented by formula (II) or optionally substituted cyclic amino

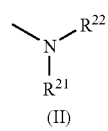
[Formula 6]
(II)

(Symbols in the formula represent the following meaning.
—$R^{21}$, —$R^{22}$:
They may be identical or different and each represent —H, lower alkyl, lower alkenyl, lower alkynyl, cycloalkyl, phenyl, heteroaryl, non-aromatic heterocyclyl, or —O-(lower alkyl), each of which is optionally substituted.)
However, when A is a ring selected from Group $X^2$ or Group $X^3$, —$R^2$ represents optionally substituted cyclic amino.
2-(2-Fluorophenyl)-N,N-dimethyl-5,7-dihydrothieno[3,4-d]pyrimidine-4-amine and 2-cyclopropyl-4-piperazin-1-yl-5,7-dihydrothieno[3,4-d]pyrimidine are excluded.]
A in formula (I) is preferably a ring selected from $X^1$, and more preferably a ring selected from Group $X^1$ in which the sulfur atom composing the ring is oxidized. The ring selected from Group $X^1$ in which the sulfur atom composing the ring is oxidized specifically includes the following:

[Formula 7]

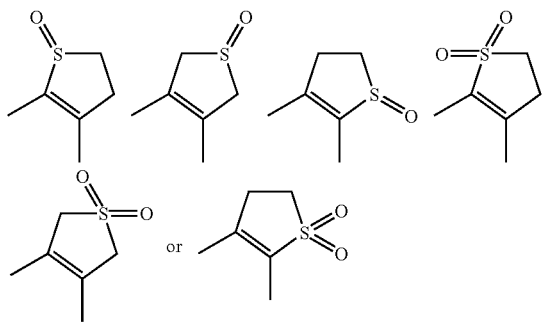

More preferably it is the ring shown below:

[Formula 8]

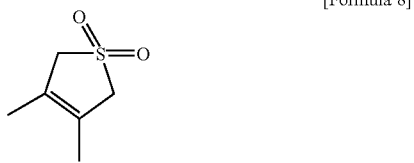

$R^1$ in formula (I) is preferably phenyl substituted with at least one halogen atom, and more preferably phenyl substituted with at least three halogen atoms. In another embodiment, $R^1$ in formula (I) is preferably cyclopropyl, cyclobutyl, cyclopentyl, cyclohexyl, or cycloheptyl, each of which is optionally substituted; more preferably cyclobutyl or cyclopentyl, each of which is optionally substituted; and further preferably cyclobutyl or cyclopentyl.

$R^2$ in formula (I) is preferably optionally substituted cyclic amino; more preferably optionally substituted piperazinyl or optionally substituted piperidinyl; and further preferably optionally substituted piperidinyl.

The condensed pyrimidine derivative represented by formula (I) is preferably a compound wherein A is a ring selected from Group $X^1$ (the sulfur atom composing the ring may be oxidized); more preferably the one wherein A is a ring selected from Group $X^1$ (the sulfur atom composing the ring may be oxidized) and $R^1$ is phenyl substituted with at least one halogen atom; further preferably the one wherein A is a ring selected from Group $X^1$ (the sulfur atom composing the ring may be oxidized) and $R^1$ is phenyl substituted with at least three halogen atoms; particularly preferably the one wherein A is a ring selected from Group $X^1$ (the sulfur atom composing the ring may be oxidized), $R^1$ is phenyl substituted with at least three halogen atoms, and $R^2$ is optionally substituted cyclic amino; and most preferably the one wherein A is a ring selected from Group $X^1$ (the sulfur atom composing the ring may be oxidized), $R^1$ is phenyl substituted with at least three halogen atoms, and $R^2$ is optionally substituted piperazinyl or optionally substituted piperidinyl.

Another embodiment of the condensed pyrimidine derivative represented by formula (I) is preferably a compound wherein A is a ring selected from Group $X^1$ (the sulfur atom composing the ring may be oxidized); more preferably the one wherein A is a ring selected from Group $X^1$ (the sulfur atom composing the ring may be oxidized) and $R^1$ is optionally substituted cyclobutyl or optionally substituted cyclopentyl; further preferably the one wherein A is a ring selected from Group $X^1$ (the sulfur atom composing the ring may be oxidized) and $R^1$ is optionally substituted cyclobutyl or optionally substituted cyclopentyl; particularly preferably the one wherein A is a ring selected from Group $X^1$ (the sulfur atom composing the ring may be oxidized), $R^1$ is optionally substituted cyclobutyl or optionally substituted cyclopentyl, and $R^2$ is optionally substituted cyclic amino; and most preferably the one wherein A is a ring selected from Group $X^1$ (the sulfur atom composing the ring may be oxidized), $R^1$ is optionally substituted cyclobutyl or optionally substituted cyclopentyl, and $R^2$ is optionally substituted piperazino or optionally substituted piperidino.

Particularly preferred compounds as the condensed pyrimidine derivative represented by formula (I) include 3-{4-[2-(4-chloro-2,5-difluorophenyl)-6,6-dioxido-5,7-dihydrothieno[3,4-d]pyrimidin-4-yl]piperazin-1-yl}propanamide, 1-[2-(4-chloro-2,5-difluorophenyl)-6,6-dioidxo-5,7-dihydrothieno[3,4-d]pyrimidin-4-yl]-4-(3-hydroxypropyl)piperidin-4-ol, N-({[1-[2-(4-chloro-2,5-difluorophenyl)-6,6-dioxido-5,7-dihydrothieno[3,4-d]pyrimidin-4-yl]piperidin-4-yl}methyl)-2-hydroxyacetamide, 3-{1-[2-(4-chloro-2,5-difluorophenyl)-6,6-dioxido-5,7-dihydrothieno[3,4-d]pyrimidin-4-yl]piperidin-4-yl}propanamide, 3-({1-[2-(4-chloro-2,5-difluorophenyl)-6,6-dioxido-5,7-dihydrothieno[3,4-d]pyrimidin-4-yl]piperidin-4-yl}amino)propan-1-ol, 3-({1-[2-(4-chloro-2,5-difluorophenyl)-6,6-dioxido-5,7-dihydrothieno[3,4-d]pyrimidin-4-yl]piperidin-4-yl}amino)propionic acid, 4-[1-(2-cyclopentyl-6,6-dioxido-5,7-dihydrothieno[3,4-d]pyrimidin-4-yl)piperidin-4-yl]butyric acid, 4-[1-(2-cyclobutyl-6,6-dioxido-5,7-dihydrothieno[3,4-d]pyrimidin-4-yl)piperidin-4-yl]butyric acid, 4-{1-[2-(4-chloro-2,5-difluorophenyl)-6,6-dioxido-5,7-dihydrothieno[3,4-d]pyrimidin-4-yl]piperidin-4-yl}butyric acid, and pharmaceutically acceptable salts thereof.

EFFECTS OF THE INVENTION

The compounds of the present invention have excellent activities in promoting insulin secretion and suppressing increase in blood glucose. Hence, the compounds of the present invention represented by formula (I), based on said activities, are effective to treat and/or prevent type 1 diabetes, type 2 diabetes, and/or insulin-resistant diseases.

Pharmacological action of the compounds of the present invention was confirmed by the following test examples.

(1) Assay for Promoting Activity on Insulin Secretion

In this assay, promoting activities on insulin secretion of the test compounds were studied using MIN6B1 cell, which was a strain of mouse pancreatic β-cells, and glibenclamide, which was a commercially available insulin secretion secretagogue, as a reference compound. The assay procedure is given below.

MIN6B1 cells were seeded on a 48-well plate at a concentration of $1 \times 10^5$ cells/well (0.25 ml) (The medium was prepared by adding FCS (fetal calf serum) to DMEM (Dulbecco's Modified Eagle Medium) containing 25 mM glucose such that the FCS concentration became 10%). After two days, the medium was suctioned by an aspirator, each well was Washed four times with 0.2 ml of KRB-HEPES buffer (Krebs-Ringer-bicarbonate-N-2-hydroxylethylpiperazine- N'-2-ethanesulfonic acid; 130 mM NaCl, 4.7 mM KCl, 1.2 mM $KH_2PO_4$, 1.2 mM $MgCl_2.6H_2O$, 0.25 mM $CaCl_2.2H_2O$, 2.5 mM $NaHCO_3$, 0.5% BSA, and 10 mM N-2-hydroxyethylpiperazine-N'-2-ethanesulfonic acid (pH 7.4)) containing 2.8 mM glucose warmed to 37° C., 0.2 ml of said buffer was again added, and the cells were incubated at 37° C. for 30 to 60 minutes. After the buffer was suctioned by an aspirator, 0.25 ml of a solution containing 10 μM of each test compound in KRB-HEPES containing 16.8 mM glucose was added to each well, and the cells were incubated at 37° C. for 22 minutes. The samples were pipetted and diluted by 25 to 51 times, and the insulin concentrations were analyzed using an insulin assay kit (Rat Insulin [$^{125}$I] Biotrak Assay System with Magnetic Separation; Amersham Bioscience K.K.). The test compounds were dissolved in 100% DMSO, and were added at the final concentration of 0.1%. The activity was expressed as a relative value, provided that insulin concentration for only DMSO was 100%. The results are shown in Table 1.

TABLE 1

| Test Compound | Promotion activity on insulin secretion, % |
|---|---|
| Example 1 | 355 |
| Example 112 | 242 |
| Example 168 | 418 |
| Example 269 | 212 |
| Example 272 | 322 |
| Example 283 | 375 |
| Example 287 | 208 |
| Example 288 | 253 |
| Example 291 | 269 |
| Example 331 | 308 |
| Example 407 | 325 |
| Glibenclamide | 122 |

As shown above, the compounds that are active ingredients of the drug of the present invention and the compounds of the present invention exhibited higher promoting activities on insulin secretion than glibenclamide, a commercially available insulin secretagogue.

(2) Oral Glucose Tolerance Test on Normal Mouse

In this assay, preventive activities of test compounds against hyperglycemia following glucose loading were examined using normal mice and nateglinide, a commercially available oral anti-hyperglycemic agent, as a reference compound. The assay procedure is given below.

ICR mice (male, six weeks old) that had been preliminary bred for one week were fasted for 18 to 20 hours to use as test animals. Each test compound was dissolved in 0.5% methylcellulose solution and orally administered at 3 mg/kg (10 mg/kg for nateglinide) before glucose loading. Timing to administer the test compound was selected to be optimal for each test compound, which was 10 minutes before glucose loading for the compounds of the present invention or 30 minutes before glucose loading for nateglinide, which was a reference compound. The hypoglycemic rate (%) at 30 minutes after glucose loading was measured relative to the control group. The results are shown in Table 2.

TABLE 2

| Test compound | Hypoglycemic rate, % |
|---|---|
| Example 50 | 37 |
| Example 460 | 30 |
| Example 442 | 36 |
| Nateglinide | 26 |

As shown above, the compounds that were active ingredients of the drug of the present invention and the compounds of the present invention exhibited more potent preventive action against hyperglycemia after glucose loading even at a lower dose than nateglinide, a commercially available oral hypoglycemic drug.

BEST MODE FOR CARRYING OUT THE INVENTION

The compounds of the present invention are further described as follows.

In the present description, "lower" means a linear or branched carbon chain with 1 to 6 carbon atoms unless otherwise noted. Therefore, "lower alkyl" means a linear or branched $C_1$-$C_6$ alkyl and specifically includes, for example, methyl, ethyl, propyl, isopropyl, butyl, isobutyl, sec-butyl, tert-butyl, pentyl, neopentyl, hexyl, and others. It is preferably a $C_1$-$C_3$ alkyl, that is, methyl, ethyl, propyl, and isopropyl. "Lower alkenyl" means a linear or branched $C_2$-$C_6$ alkenyl and specifically includes, for example, vinyl, allyl, butenyl, and others. "Lower alkynyl" means a linear or branched $C_2$-$C_6$ alkynyl and specifically includes, for example, propargyl and others. "Lower alkylidene" means a linear or branched $C_1$-$C_6$ alkylidene and specifically includes, for example, methylidene, ethylidene, propylidene, and others.

"Halogen atom" means fluoro, chloro, bromo, or iodo. It is preferably fluoro, chloro, or bromo.

"Cyclic amino" means a monovalent group derived from three- to eight-membered non-aromatic cyclic amine that contains at least one nitrogen atom and optionally contains one or more identical or different additional heteroatoms selected from the group consisting of nitrogen, oxygen, and sulfur, wherein the nitrogen atom necessarily present in said ring is the bonding site. The sulfur atom on the ring in said cyclic amino may be oxidized. Specific examples include monovalent groups derived from azetidine, pyrrolidine, piperidine, azepane, azocane, piperazine, homopiperazine, morpholine, oxazepane, thiomorpholine, thiazepane, and others. These rings may contain (an) unsaturated bond(s) in part of the ring, such as dihydropyrrole, tetrahydropyridine, tetrahydroazepine, imidazolidine, oxazolidine, dihydrooxazine, thiazolidine, dihydrothiazine, and others. These rings may be condensed with a cycloalkane moiety, such as decahydroquinoline, decahydroisoquinoline, and others. These rings may be condensed with a benzene ring, such as indoline, 1,2,3,4-tetrahydroquinoline, 1,2,3,4-tetrahydroisoquinoline, and others. These rings may be condensed with another cyclic amine moiety such as octahydroimidazo[1,5-a]pyrazine, octahydro[1,2-a]pyrazine, and others. These rings may be condensed with an aromatic heterocycle, such as 2,3,4,9-tetrahydro-1H-β-carboline, 4,5,6,7-tetrahydro-1H-pyrazolo[4,3-c]pyridine, 4,5,6,7-tetrahydro-2H-pyrazolo[4,3-c]pyridine, 5,6,7,8-tetrahydro-pyrido[4,3-d]pyrimidine, and others. These rings may be spiro-condensed with a non-aromatic heterocycle, such as 1,3,8-triazaspiro[4.5]decane, 1-oxa-8-azaspiro[4.5]decane, 1,4-dioxa-8-azaspiro[4.5]decane, 2,4-dioxa-9-azaspiro[5.5]undecane, 2,8-diazaspiro[4.5]decane, and others. These rings may be bridged cyclic amino, such as monovalent groups derived from 2,5-diazabicyclo[2.2.1]heptane, 2,5-diazabicyclo[2.2.2]octane, and others.

"Cycloalkyl" means a three- to eight-membered carbocycle, which may be partially unsaturated. Specific examples include cyclopropyl, cyclopentyl, cyclohexyl, cyclooctyl, cyclobutenyl, cyclohexenyl, cyclooctadienyl, and others. These rings may be condensed with a benzene ring.

"Heteroaryl" means a monovalent group derived from a five- to six-membered aromatic heterocycle containing one or more identical or different heteroatoms selected from the group consisting of nitrogen, oxygen, and sulfur. Specific examples include monovalent groups derived from pyrrole, pyridine, pyrazole, imidazole, pyridazine, pyrimidine, pyrazine, triazole, triazine, tetrazole, furan, thiophene, oxazole, thiazole, oxadiazole, thiadiazole, and others. These rings may be condensed with a benzene ring, such as indole, indazole, quinoline, and others, or may be partially hydrogenated, as tetrahydropyridine, tetrahydroazepine, dihydropyridine, indoline, and others.

"Non-aromatic heterocyclyl" means a monovalent group derived from a five- to six-membered saturated heterocycle containing one or more identical or different heteroatoms selected from the group consisting of nitrogen, oxygen, and optionally oxidized sulfur. Specific examples include, in addition to the above cyclic amino, monovalent groups in which an atom other than the nitrogen atom in the above cyclic amino is the bonding site, and monovalent groups derived from tetrahydrofuran, tetrahydropyran, tetrahydrothiofuran, tetrahydrothiopyran, dioxolane, 1,3-dioxane, 1,4-dioxane, and others. These rings may be bridged, such as 1-azabicyclo[2.2.1]heptane, quinuclidine, and others.

"Bridged cyclic amino" means a monovalent group in which two non-adjacent carbon atoms composing the ring in the above cyclic amino are bridged by methylene, ethylene, or trimethylene.

In "optionally substituted" or "substituted" group in the present specification, any substituent commonly found as a substituent on said group may be present. One or more of these substituents may be present on each group.

In "phenyl substituted with at least one halogen atom, which may have (an) additional substituent(s)" represented by $R^1$, "cyclopropyl, cyclobutyl, cyclopentyl, cyclohexyl, or cycloheptyl, each of which is optionally substituted" represented by $R^1$, "optionally substituted cyclic amino" represented by $R^2$, and "cycloalkyl, phenyl, heteroaryl, or non-aromatic heterocyclyl, each of which is optionally substituted" represented by $R^{21}$ or $R^{22}$, allowable substituents include groups given in (a) to (h) below. "$R^z$" represents lower alkyl optionally substituted with one or more groups selected from the group consisting of —OH, —O-(lower alkyl), —OCO-(lower alkyl), carboxyl, —CO$_2$-(lower alkyl), —CO-(lower alkyl), carbamoyl optionally substituted with one or two lower alkyls, cyano, amino optionally substituted with one or two lower alkyls, phenyl, heteroaryl, cycloalkyl, non-aromatic heterocyclyl, and halogen atom.

(a) Halogen atom;
(b) —OH, —O—$R^z$, —O-phenyl, —OCO—$R^z$, —OCONH—$R^z$, and oxo (=O);
(c) —SH, —S—$R^z$, —S-phenyl, —S-heteroaryl, —SO—$R^z$, —SO-phenyl, —SO-heteroaryl, —SO$_3$H, —SO$_2$—$R^z$, —SO$_2$-phenyl optionally substituted with lower alkyl, —SO$_2$-heteroaryl optionally substituted with lower alkyl, and sulfamoyl optionally substituted with one or two $R^z$s;
(d) Amino optionally substituted with one or two $R^z$s, —NHCO—$R^z$, —NHCO-phenyl, —NHCO$_2$—$R^z$, —NHCONH$_2$, —NHCONH—$R^z$, —NHSO$_2$—$R^z$, —NHSO$_2$-phenyl, wherein the phenyl is optionally substituted with lower alkyl, —NHSO$_2$NH$_2$, and nitro;
(e) —CHO, —CO—$R^z$, —CO$_2$H, —CO$_2$—$R^z$, carbamoyl optionally substituted with one or two $R^z$s, —CO-cyclic amino) optionally substituted with —OH or oxo, —COCO—$R^z$, and cyano;

(f) Phenyl or cycloalkyl each of which is optionally substituted with one or more groups selected from the group consisting of —OH, —O-(lower alkyl), oxo, —S-(lower alkyl), amino optionally substituted with one or two lower alkyls, cyclic amino, —CO$_2$H, carbamoyl optionally substituted with one or two $R^z$s, halogen atom, and $R^z$;
(g) Heteroaryl or non-aromatic heterocyclyl each of which is optionally substituted with —OH, —O-(lower alkyl), oxo, —S-(lower alkyl), amino optionally substituted with one or two lower alkyls, cyclic amino, —CO$_2$H, carbamoyl optionally substituted with one or two $R^z$s, halogen atom, and $R^z$; and
(h) Lower alkyl, lower alkenyl, or lower alkylidene each of which may be substituted with one or more groups selected from the substituents given in (a) to (g) above.

In "lower alkyl, lower alkenyl, lower alkynyl, or —O-(lower alkyl) each of which is optionally substituted" represented by $R^{21}$ or $R^{22}$, allowable substituents include the groups given in (a) to (g) above.

The compounds of the present invention represented by formula (I) may have (an) asymmetric carbon atom(s) depending on the substituents and optical isomers may exist based on this fact. The present invention encompasses all of mixtures and isolated compounds of these optical isomers. The compounds of the present invention may exist in a form of tautomers. Any separated tautomers and mixtures thereof are included in the present invention. The present invention also encompasses labeled species, that is, compounds in which one or more atoms in the compounds of the present invention are replaced by a radioactive isotope or non-radioactive isotope.

The compounds of the present invention may form a salt, which is encompassed in the present invention so far as such salt is pharmaceutically acceptable. Said salts specifically include salts with an inorganic acid such as hydrochloric acid, hydrobromic acid, hydroiodic acid, sulfuric acid, nitric acid, and phosphoric acid; salts with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, p-toluenesulfonic acid, aspartic acid, and glutamic acid; salts with an inorganic base containing a metal such as sodium, potassium, calcium, and magnesium; salts with an organic base such as methylamine, ethylamine, ethanolamine, lysine, and ornithine; ammonium salt, and others. Furthermore, the present invention encompasses various hydrates, solvates, and all crystal polymorphs of the compounds of the present invention and pharmaceutically acceptable salts thereof. The present invention encompasses all of so-called prodrugs, that is, compounds that are metabolized in vivo to be converted into the compounds represented by formula (I) or salts thereof. As groups used for forming the prodrugs of the present invention, there may be mentioned groups described in Prog. Med., 5, 2157-2161 (1985) and in "Development of Drugs," Vol. 7 "Molecular Design," pp. 163-198, Hirokawa Shoten (1990).

The compounds of the present invention and pharmaceutically acceptable salts thereof can be manufactured by applying various known synthetic methods utilizing characteristics based on the skeletal structure thereof or type of substituents. Typical preparation methods are illustrated below. They can be also manufactured according to the description in Reference Examples and Examples described hereinafter or by similar methods thereto. Depending on properties of functional groups, it is sometimes advantageous in manufacturing techniques that said functional group is replaced with an appropriate protective group, that is, group readily convertible to said functional group, in a stage of starting material or intermediate. The protective group is thereafter removed as needed to obtain desired compounds. Such functional groups include hydroxyl, carboxyl, amino, and others. Protective groups therefor include, for example, groups described in Greene and Wuts, "Protective Groups in Organic Synthesis (third edition)", which may be used as appropriate according to reaction conditions to be employed.

[Formula 9]

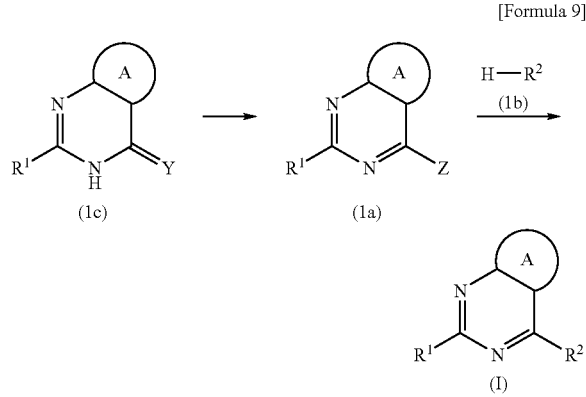

(In the scheme, ring A, $R^1$, and $R^2$ represent the same meaning as the above, Y represents O or S, and Z represents a leaving group. Ditto hereinafter.)

The present preparation method is a method in which an aromatic ring-condensed pyrimidine derivative having a leaving group represented by formula (1a) is reacted with an amine derivative represented by formula (1b) to manufacture the compound of the present invention represented by general formula (I).

The leaving group represented by Z in compound (1a) means a group that can be eliminated together with the hydrogen atom of the amino group in compound (1b) in a form of HZ under the reaction condition. Examples thereof include halogen atoms such as fluoro, chloro, bromo, and iodo, lower alkylsulfonyloxy groups such as methanesulfonyloxy, trihalomethanesulfonyloxy groups such as trifluoromethanesulfonyloxy, arylsulfonyloxy groups such as benzenesulfonyloxy and p-toluenesulfonyloxy, and others.

The reaction of compound (1a) with compound (1b) is conducted under normal or positive pressure in the absence of solvent or in an appropriate solvent.

Specific examples of the solvent include aromatic hydrocarbons such as toluene and xylene; ketones such as methyl ethyl ketone and methyl isobutyl ketone; ethers such as ether, tetrahydrofuran (THF), dioxane, and diglyme; alcohols such as methanol (MeOH), ethanol (EtOH), and 2-propanol (iPrOH); acetonitrile, dimethylformamide (DMF), 1,3-dimethyl-2-imidazolidinone (DMI), dimethylsulfoxide (DMSO), water, and mixtures thereof. The present reaction is preferably performed in the presence of a base, which specifically includes alkali carbonates such as sodium carbonate and potassium carbonate, alkali hydrogencarbonates such as sodium hydrogencarbonate and potassium hydrogencarbonate; tertiary amines such as triethylamine and diisopropylethylamine; and others. Excess amount of compound (1b) may be used to function as a base. The reaction temperature is generally about 20° C. to about 180° C., and preferably about 60° C. to about 130° C., depending on the starting compounds, reaction conditions, and others.

Compound (1a) can be synthesized, for example, by halogenating or sulfonylating a pyrimidinone or pyrimidinethione derivative represented by formula (1c) according to common procedures.

Halogenation in the present reaction is carried out, for example, by reacting compound (1c) with a halogenating agent such as phosphorous oxychloride and phosphorous tribromide. Sulfonylation is carried out, for example, by reacting compound (1c) in which Y is an oxygen atom with a sulfonylating agent such as methanesulfonyl chloride, p-toluenesulfonyl chloride, trifluoromethanesulfonyl chloride, and trifluoromethanesulfonic anhydride.

Compound (1c) can be synthesized by a known method, for example, the methods described in J. Am. Chem. Soc., 74, 842 (1952), Chem. Ber., 95, 937 (1962), or J. Org. Chem., 29, 2887 (1964) or similar methods thereto. Compound (1b) is commercially available or can be synthesized by a known method.

Some compounds of the present invention can be manufactured from another compound of the present invention manufactured by the above preparation method, methods described in Examples, methods obvious to those skilled in the art, or variation thereof, through procedures generally used by those skilled in the art such as alkylation, acylation, substitution reaction, oxidation, reduction, and hydrolysis, which are publicly known.

The compounds of the present invention thus manufactured are purified for isolation as a free form or a salt after converting to a salt by known treatment. Isolation and purification are performed using common chemical operations such as extraction, concentration, evaporation, crystallization, filtration, recrystallization, and various chromatographic techniques.

When the compound of the present invention has an asymmetric carbon, there are optical isomers. Such optical isomers can be resolved by a common method such as fractional crystallization, in which an appropriate salt is recrystallized, and column chromatography. Optically active compounds can be also manufactured using appropriate optically active starting materials.

The drugs of the present invention can be prepared by a common method using one or more compounds of the present invention and carriers for drugs, excipients, or other additives commonly used in preparation. Administration may be in either form of oral administration of tablets, pills, capsules, granules, powder, liquids, or the like, or parenteral administration of injections such as intravenous injection and intramuscular injection or suppositories, transnasal, transmucosal, or percutaneous administration, or the like.

Solid compositions used for oral administration in the present invention include tablets, powder, granules, and others. In such solid compositions, one or more active substances are mixed with at least one inert diluent such as lactose, mannitol, glucose, hydroxypropylcellulose, microcrystalline cellulose, starch, polyvinylpyrrolidone, and magnesium aluminometasilicate. Such compositions may contain, according to a common method, additives other than inert diluents, for example, lubricants such as magnesium stearate, disintegrating agents such as calcium cellulose glycolate, stabilizers, solubilizing agents, and others. Tablets or pills may be coated as needed with sugar coating or gastric soluble or enteric film such as sucrose, gelatin, hydroxypropylcellulose, and hydroxypropylmethylcellulose phthalate.

Liquid compositions for oral administration include pharmaceutically acceptable emulsion, liquid, suspension, syrup, elixir, and others. The composition contains a common inert diluent, for example, purified water or ethanol (EtOH). Such composition may contain, besides inert diluents, adjuvants such as wetting agents and suspending agents, sweeteners, flavor, fragrances, and preservatives.

Injections for parenteral administration contain sterile aqueous or non-aqueous solvent, suspension medium, or emulsifying medium. Aqueous solvent or suspension medium includes, for example, distilled water for injection and physiological saline. Non-aqueous solvent or suspension medium includes, for example, propylene glycol, polyethylene glycol, vegetable oils such as olive oil, alcohols such as EtOH and polysorbate 80 (Pharmacopoeia name), and others. Such compositions may further contain adjuvants such as preservatives, wetting agents, emulsifiers, dispersants, stabilizers, and solubilizing agents. These are sterilized, for example, by passing through a sterile bacteria filter, formulating with a bactericide, or radiation. These may be also used after manufacturing a sterile solid composition, which is dissolved in sterile water or a sterile solvent for injection prior to use.

The proper dose per day in oral administration is generally about 0.0001 to 50 mg/kg of body weight, preferably about 0.001 to 10 mg/kg, and more preferably 0.01 to 1 mg/kg, which is administered once or dividedly into two to four times. The proper dose per day in intravenous administration is about 0.0001 to 1 mg/kg of body weight, and preferably about 0.001 to 0.1 mg/kg, which is administered once per day or dividedly into multiple times per day. The dose is properly determined in accordance with each case considering symptom, age, sex, and others.

EXAMPLES

The present invention is specifically described in accordance with Examples hereinafter, but not limited in any way by these Examples. Some starting compounds used in Examples are new substances and methods for manufacturing them from known substances are described as Reference Examples.

Reference Example 1

A chloroform-EtOH solution of 4-chloro-2,5-difluorobenzonitrile was saturated with hydrogen chloride by bubbling, stirred at ambient temperature for 16 hours, and then concentrated to yield an imidate, which was stirred together with ammonium carbonate in EtOH at ambient temperature for 3 days to yield 4-chloro-2,5-difluorobenzenecarboxamidine.

Compounds shown in Table 3 below were prepared similarly to Reference Example 1. Symbols in Table represent the following meaning (ditto hereinafter).
Rf: Reference Example number
Data: Spectral data (MS: FAB-MS (M+H)$^+$, MM: FAB-MS (M)$^+$, MN: FAB-MS (M−H)$^−$, ME: ES-MS (M+H)$^+$, MF: ES-MS (M)$^+$, MG: ES-MS (M)$^−$, MH: ES-MS (M−H)$^−$, MI: EI-MS (M+H)$^+$, MJ: EI-MS (M)$^+$, MA: APCI-MS (M+H)$^+$)
Structure: Chemical Structural Formula
R, R$^1$, R$^2$: Substituents in general formula (Me, methyl, Et; ethyl, cPen; cyclopentyl, cHex; cyclohexyl, pyrr; pyrrolidin-1-yl, pipe; piperidin-1-yl, hPy; 1,2,3,6-tetrahydropyridin-1-yl, azep; azepan-1-yl, pipa; piperazin-1-yl, mor; morpholin-4-yl, hpipa; homopiperazin-1-yl, fur; furyl, Py; pyridyl, Pyox; 1-oxidopyridyl, tmor; thiomorpholin-4-yl, Ph; phenyl, Ms; methanesulfonyl, Boc; tert-butyloxycarbonyl, Ac; acetyl. di; di, tri; tri. The number preceding the substituent symbol represents the position of substitution and hence, for example, 4-(4-Py)-pipa means 4-pyridin-4-ylpiperazin-1-yl.)

TABLE 3

| Rf | Structure | Data |
|---|---|---|
| 1 | F, Cl, F substituted benzenecarboxamidine | MS: 191 |
| 1-1 | F, F, F substituted benzenecarboxamidine | ME: 175 |
| 1-2 | F, Br, F substituted benzenecarboxamidine | MJ: 234, 236 |
| 1-3 | F, F, F substituted benzenecarboxamidine | 176 [ES-MS(M + 2H)$^+$] |
| 1-4 | F, Cl, F substituted benzenecarboxamidine | MS: 191 |
| 1-5 | F, Br, F substituted benzenecarboxamidine | MS: 235 |

Reference Example 2

A mixture of 2-chloroisonicotinonitrile, trimethylaluminum (1.01-M hexane solution), ammonium chloride, and toluene was heated under reflux with stirring for 14 hours to yield 2-chloropyridine-3-carboxamidine.
ME: 156

Reference Example 3

A mixture of methyl 2,5-dichlorothiophene-3-carboxylate, trimethylaluminum (1.01-M hexane solution), ammonium chloride, and toluene was heated under reflux with stirring for 3 days to yield 2,5-dichlorothiophene-3-carboxamidine.
MF: 196

Reference Example 4

A mixture of 4-chloro-2,5-difluorobenzenecarboxamidine, ethyl 4-oxotetrahydrothiophene-3-carboxylate, NaOMe, and MeOH was stirred at ambient temperature for 19 hours and then at 60° C. for 5 hours to yield 2-(4-chloro-2,5-difluorophenyl)-5,7-dihydrothieno[3,4-d]pyrimidin-4(1H)-one.

Compounds given in Tables 4 and 5 below were prepared similarly to Reference Example 4.

TABLE 4

| Rf | Structure | Data |
|---|---|---|
| 4 | 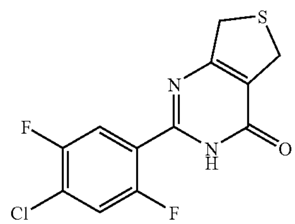 | MS: 301 |
| 4-1 | 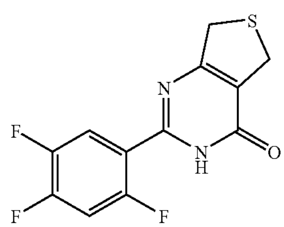 | ME: 285 |
| 4-2 | 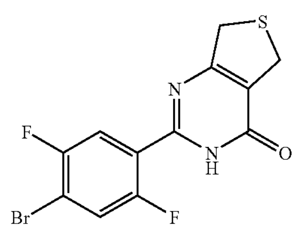 | MF: 346 |
| 4-3 | 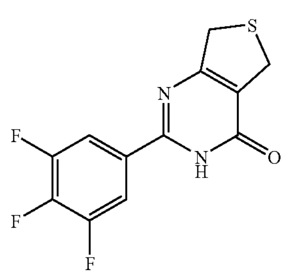 | MS: 285 |
| 4-4 | 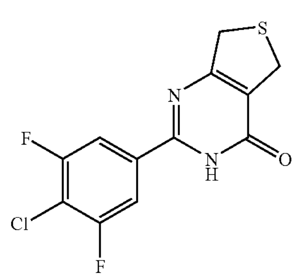 | MS: 301 |

TABLE 4-continued

| Rf | Structure | Data |
|---|---|---|
| 4-5 | 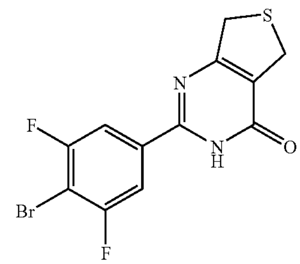 | MN: 343 |
| 4-6 | 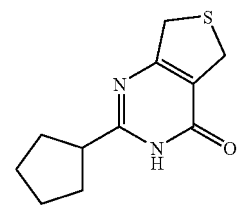 | ME: 223 |
| 4-7 | 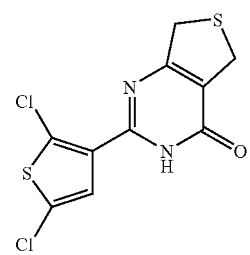 | MG: 304 |
| 4-8 | 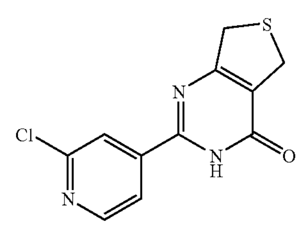 | MH: 264 |
| 4-9 | 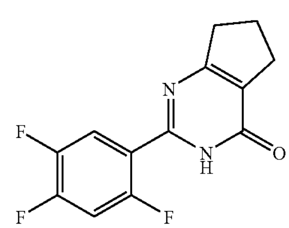 | ME: 267 |
| 4-10 | 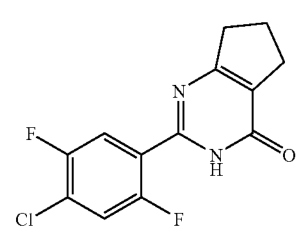 | ME: 283 |

TABLE 4-continued

| Rf | Structure | Data |
|---|---|---|
| 4-11 | 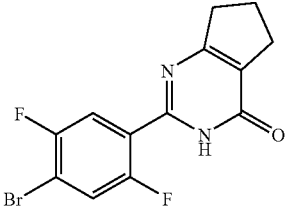 | ME: 327 |
| 4-12 | 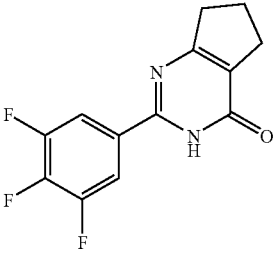 | ME: 267 |
| 4-13 | 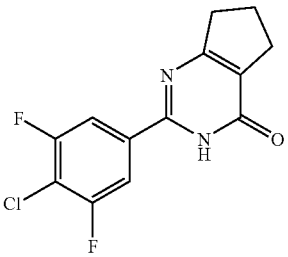 | MS: 283 |

TABLE 5

| Rf | Structure | Data |
|---|---|---|
| 4-14 | 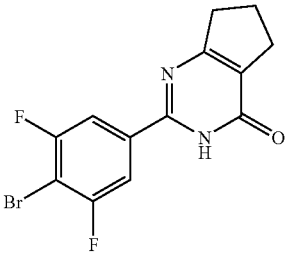 | MS: 327 |
| 4-15 | 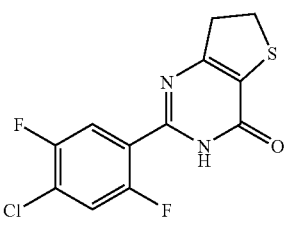 | MS: 301 |
| 4-16 | 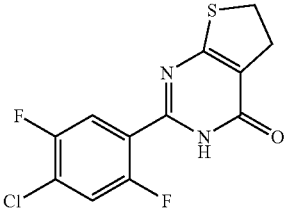 | MS: ? |

TABLE 5-continued

| Rf | Structure | Data |
|---|---|---|
| 4-17 | 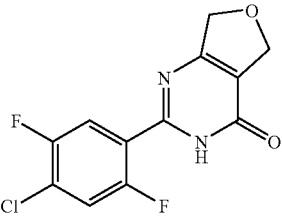 | ME: 285 |
| 4-18 | 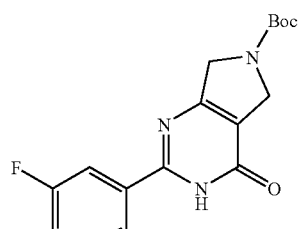 | MS: 384 |
| 4-19 | 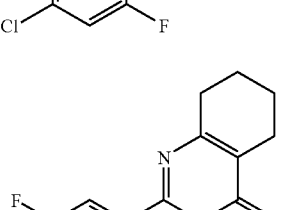 | |
| 4-20 | 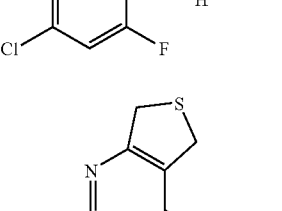 | |

Reference Example 5

To a mixture of tert-butyl 2-(4-chloro-2,5-difluorophenyl)-4-oxo-3,5,6,7-tetrahydro-4H-pyrrolo[3,4-d]pyrimidine-6-carboxylate, chloroform, and MeOH, 4M hydrogen chloride (HCl) in ethyl acetate (EtOAc) solution was added, and the resultant mixture was stirred at ambient temperature for 5 hours to yield 2-(4-chloro-2,5-difluorophenyl)-3,5,6,7-tetrahydro-4H-pyrrolo[3,4-d]pyrimidin-4-one hydrochloride.

MS: 284

Reference Example 6

A mixture of 2-(4-chloro-2,5-difluorophenyl)-5,7-dihydrothieno[3,4-d]pyrimidin-4(1H)-one and phosphorous oxychloride was stirred at 90° C. for 4 hours to yield 4-chloro-2-(4-chloro-2,5-difluorophenyl)-5,7-dihydrothieno[3,4-d]pyrimidine.

Compounds given in Tables 6 and 7 below were prepared similarly to Reference Example 6.

TABLE 6

| Rf | Structure | Data |
|---|---|---|
| 6 | 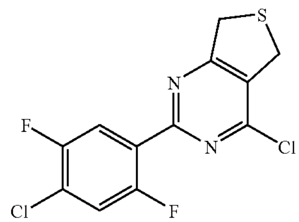 | MS: 319 |
| 6-1 | 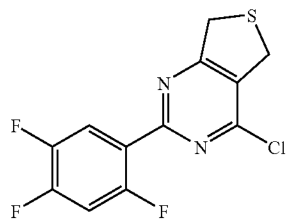 | MA: 303 |
| 6-2 | 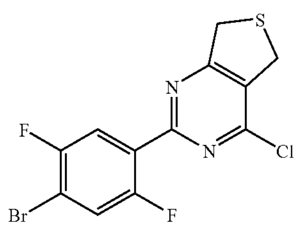 | MA: 364 |
| 6-3 | 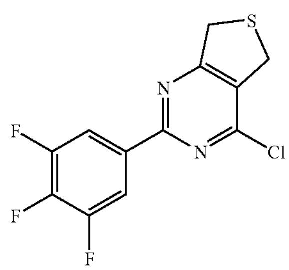 | MS: 303 |
| 6-4 | 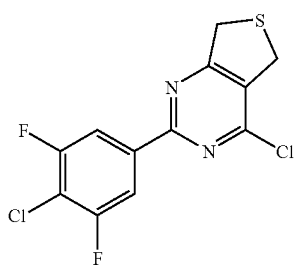 | MS: 319 |
| 6-5 | 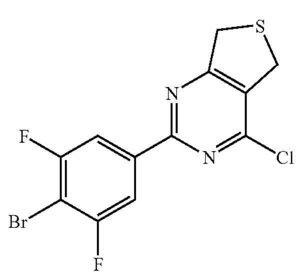 | MI: 364 |
| 6-6 | | ME: 241 |
| 6-7 | | MS: 323 |
| 6-8 | | MS: 284 |
| 6-9 | | ME: 285 |
| 6-10 | | ME: 301 |
| 6-11 | | ME: 345 |

TABLE 6-continued

| Rf | Structure | Data |
|---|---|---|
| 6-12 | 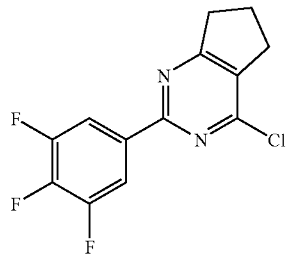 | ME: 285 |
| 6-13 | 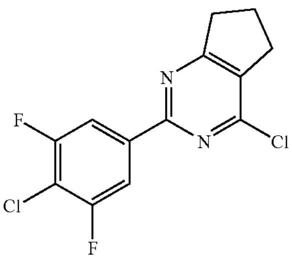 | MS: 301 |

TABLE 7

| Rf | Structure | Data |
|---|---|---|
| 6-14 | 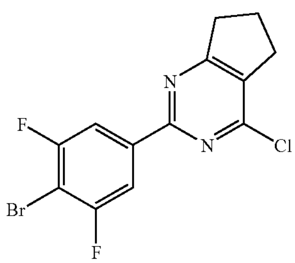 | MS: 347 |
| 6-15 | 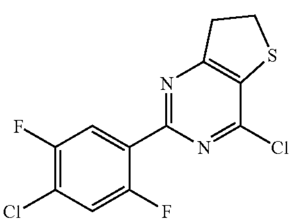 | ME: 319 |
| 6-16 | 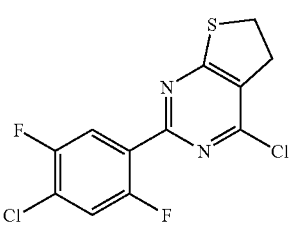 | MS: 319 |
| 6-17 | 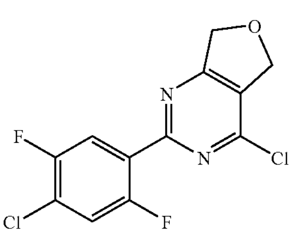 | MS: 303 |
| 6-18 | | |
| 6-19 | | |

Reference Example 7

A methylene chloride solution of 2-(4-chloro-2,5-difluorophenyl)-3,5,6,7-tetrahydro-4H-pyrrolo[3,4-d]pyrimidin-4-one hydrochloride, triethylamine, and methanesulfonyl chloride was stirred at ambient temperature for 3 hours to yield 2-(4-chloro-2,5-difluorophenyl)-6-(methylsulfonyl)-6,7-dihydro-H-pyrrolo[3,4-d]pyrimidin-4-yl methanesulfonate.

Compounds given in Table 8 below were prepared similarly to Reference Example 7.

TABLE 8

| Rf | Structure | Data |
|---|---|---|
| 7 | 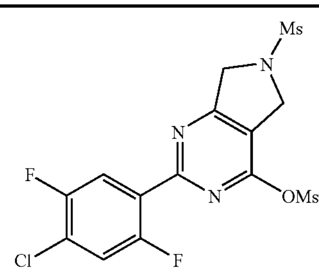 | MS: 440 |
| 7-1 | 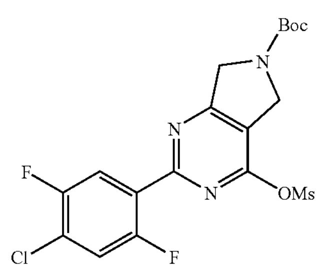 | MS: 462 |

Reference Example 8

A mixture of 4-chloro-2-(4-chloro-2,5-difluorophenyl)-5,7-dihydrothieno[3,4-d]pyrimidine, m-chloroperbenzoic acid, and chloroform was stirred at ambient temperature for 1 hour to yield 4-chloro-2-(4-chloro-2,5-difluorophenyl)-5,7-dihydrothieno[3,4-d]pyrimidine 6,6-dioxide.

Compounds given in Table 9 below were prepared similarly to Reference Example 8.

TABLE 9

| Rf | Structure | Data |
|---|---|---|
| 8 | 2-(4-chloro-2-fluoro-5-fluorophenyl)-4-chloro-thieno[3,4-d]pyrimidine 6,6-dioxide | MS: 351 |
| 8-1 | 2-(2,4,5-trifluorophenyl)-4-chloro-thieno[3,4-d]pyrimidine 6,6-dioxide | MS: 335 |
| 8-2 | 2-(4-bromo-2,5-difluorophenyl)-4-chloro-thieno[3,4-d]pyrimidine 6,6-dioxide | MM: 396 |
| 8-3 | 2-(3,4,5-trifluorophenyl)-4-chloro-thieno[3,4-d]pyrimidine 6,6-dioxide | MS: 335 |
| 8-4 | 2-(3-chloro-4,5-difluorophenyl)-4-chloro-thieno[3,4-d]pyrimidine 6,6-dioxide | MS: 351 |

TABLE 9-continued

| Rf | Structure | Data |
|---|---|---|
| 8-5 | 2-(4-bromo-3,5-difluorophenyl)-4-chloro-thieno[3,4-d]pyrimidine 6,6-dioxide | MS: 397 |
| 8-6 | 2-cyclopentyl-4-chloro-thieno[3,4-d]pyrimidine 6,6-dioxide | ME: 273 |
| 8-7 | 2-(2,5-dichlorothien-3-yl)-4-chloro-thieno[3,4-d]pyrimidine 6,6-dioxide | MG: 354 |
| 8-8 | 2-(2-chloropyridin-4-yl)-4-chloro-thieno[3,4-d]pyrimidine 6,6-dioxide | MH: 314 |
| 8-9 | 2-(4-chloro-2-fluoro-5-fluorophenyl)-4-chloro-6,7-dihydro-thieno[3,2-d]pyrimidine 5,5-dioxide | ME: 351 |
| 8-10 | 2-cyclopropyl-4-chloro-thieno[3,4-d]pyrimidine 6,6-dioxide | MS: 245 |

TABLE 9-continued

| Rf | Structure | Data |
| --- | --- | --- |
| 8-11 | (structure: 2-cyclobutyl-4-chloro thieno[3,4-d]pyrimidine with sulfone S(=O)₂) | MJ: 258 |

Reference Example 9

A tert-butanol solution of N-methylmorpholine-N-oxide and osmium tetraoxide was added to a mixture of 1-benzyl-4-methyleneazepane hydrochloride and THF-water, and the resultant solution was stirred at ambient temperature for 24 hours and then treated with 4M HCl-EtOAc solution to yield 1-benzyl-4-(hydroxymethyl)azepan-4-ol hydrochloride. To an EtOH solution of 1-benzyl-4-(hydroxymethyl)azepan-4-ol hydrochloride obtained was added 10% palladium on activated carbon, and the suspension was stirred under hydrogen atmosphere at ambient temperature for 6 hours to yield 4-(hydroxymethyl)azepan-4-ol hydrochloride.
MS: 146

Reference Example 10

Sodium hydride and 1-benzylazepan-3-one were added to a THF solution of ethyl diethoxyphosphorylacetate with ice-cooling, and the mixture was stirred at ambient temperature for 2 hours to yield a stereoisomeric mixture of ethyl (1-benzylazepan-3-ylidene)acetate, which was treated with 4M HCl-EtOAc solution, followed by adding EtOH and 10% palladium on activated carbon and stirring under hydrogen atmosphere at ambient temperature for 15 hours to yield ethyl azepan-3-ylacetate hydrochloride.
MS: 186

Reference Example 11

A mixture of 1-tert-butoxycarbonylpiperidin-4-ol, sodium hydride, and DMF was stirred at ambient temperature for 5 minutes, here was added 2-chloro-N,N-dimethylethylamine, and the mixture was further stirred at ambient temperature for 30 minutes to yield 2-[(1-tert-butoxycarbonylpiperidin-4-yl)oxy]-N,N-dimethylethylamine, which was stirred together with 4M HCl-dioxane solution at ambient temperature for 7 hours to yield N,N-dimethyl-2-(piperidin-4-yloxy)ethylamine dihydrochloride.
MS: 273

Reference Example 12

A mixture of 1-tert-butoxycarbonylpiperidin-4-ol, triethylamine, benzenesulfonyl chloride, and methylene chloride was stirred at ambient temperature for 2 days to yield 1-tert-butoxycarbonylpiperidin-4-yl benzenesulfonate. A mixture of 1-tert-butoxycarbonylpiperidin-4-yl benzenesulfonate obtained, diethyl malonate, 20% NaOEt-EtOH, and EtOH was heated under reflux with stirring for 22 hours to yield diethyl[1-(tert-butoxycarbonyl)piperidin-4-yl]malonate. A mixture of diethyl [1-(tert-butoxycarbonyl)piperidin-4-yl] malonate obtained, lithium borohydride, toluene, and THF was stirred at 60° C. for 18 hours to yield 2-(1-tert-butoxycarbonylpiperidin-4-yl)propane-1,3-diol, which was stirred together with 4M HCl-dioxane solution in MeOH at ambient temperature for 1 hour to yield 2-piperidin-4-ylpropane-1,3-diol hydrochloride.
MS: 160

Reference Example 13

A mixture of (1-tert-butoxycarbonylpiperidine-4,4-diyl)dimethanol, 4M HCl-dioxane solution, and MeOH was stirred at ambient temperature for 2 hours to yield (piperidine-4,4-diyl)dimethanol hydrochloride.
MS: 146

Reference Example 14

A mixture of 1-tert-butoxycarbonyl-4-(3-hydroxypropyl)piperidin-4-ol and 4M HCl-dioxane solution was stirred at ambient temperature for 3.5 hours to yield 4-(3-hydroxypropyl)piperidin-4-ol hydrochloride.
MS: 160

Reference Example 15

A mixture of 1-tert-butoxycarbonylpiperidin-4-one and N,N-dimethylformamide dimethylacetal was heated under reflux with stirring for 6 hours to yield 1-tert-butoxycarbonyl-3-[(dimethylamino)methylene]piperidin-4-one. A mixture of 1-tert-butoxycarbonyl-3-[(dimethylamino)methylene]piperidin-4-one obtained, 2-hydrazinoethanol, and MeOH was heated under reflux with stirring for 2 hours to yield a mixture of 2-(5-tert-butoxycarbonyl-4,5,6,7-tetrahydro-2H-pyrazolo[4,3-c]pyridin-2-yl)ethanol and 2-(5-tert-butoxycarbonyl-4,5,6,7-tetrahydro-1H-pyrazolo[4,3-c]pyridin-1-yl)ethanol. A mixture of the compounds obtained, 4M HCl-EtOAc solution, and EtOH was stirred at ambient temperature for 2 hours to yield a mixture of 2-(4,5,6,7-tetrahydro-2H-pyrazolo[4,3-c]pyridin-2-yl)ethanol dihydrochloride and 2-(4,5,6,7-tetrahydro-1H-pyrazolo[4,3-c]pyridin-1-yl)ethanol dihydrochloride.
ME: 168

Reference Example 16

A mixture of ethyl (2E)-(1-benzyl-3-methylpiperidin-4-ylidene)acetate, 1-chloroethyl chloroformate, and 1,2-dichloroethane was heated under reflux with stirring for 30 minutes and then concentrated under reduced pressure. The residue was dissolved in EtOH and the solution was heated under reflux with stirring for 10 minutes to yield ethyl (2E)-(3-methylpiperidin-4-ylidene)acetate.
MS: 184

Reference Example 17

A mixture of 1-tert-butoxycarbonylpiperazine, 3-hydroxypropionic acid, 1-hydroxybenzotriazole (HOBt), 1-ethyl-3-(3-dimethylaminopropyl)carbodiimide hydrochloride (EDCI), and DMF was stirred at ambient temperature for 24 hours to yield 3-(4-tert-butoxycarbonylpiperazin-1-yl)-3-oxopropan-1-ol, which was stirred together with 4M HCl-dioxane solution and MeOH at ambient temperature for 16 hours to yield 3-oxo-3-piperazin-1-ylpropan-1-ol hydrochloride.
MS: 159

Reference Example 18

A mixture of N-(2-nitrobenzenesulfonyl)ethylenediamine, 2-chloroethanesulfonyl chloride, triethylamine, and methylene chloride was stirred at 0° C. for 3 hours to yield N-(2-{[(2-chloroethyl)sulfonyl]amino}ethyl)-2-nitrobenzenesulfonamide. This compound was dissolved in acetonitrile, here were added cesium carbonate and tetrabutylammonium iodide, and the mixture was stirred at 80° C. for 21 hours to yield 5-[(2-nitrophenyl)sulfonyl]-1,2,5-thiadiazepane 1,1-dioxide. This compound was dissolved in acetonitrile, here were added 4-methylbenzenethiol and potassium carbonate, and the mixture was stirred at 50° C. for 21 hours to yield 1,2,5-thiadiazepane 1,1-dioxide.

Reference Example 19

A mixture of N-(2-nitrobenzenesulfonyl)ethylenediamine, 3-hydroxy-2,2-dimethylpropionic acid, EDCI, HOBt, methylene chloride, and DMF was stirred at ambient temperature for 4 hours to yield 3-hydroxy-2,2-dimethyl-N-(2-{[(2-nitrophenyl)sulfonyl]amino}ethyl)propanamide. A mixture of this compound, triphenylphosphine, a toluene solution of diethyl azodicarboxylate, and THF was stirred at 0° C. for 15 hours to yield 6,6-dimethyl-1-[(2-nitrophenyl)sulfonyl]-1,4-diazepan-5-one. A mixture of this compound, 4-methylbenzenethiol, potassium carbonate, and acetonitrile was stirred at ambient temperature for 3 hours to yield 6,6-dimethyl-1,4-diazepan-5-one.

Example 1

A mixture of 410 mg of 4-chloro-2-(4-chloro-2,5-difluorophenyl)-5,7-dihydrothieno[3,4-d]pyrimidine 6,6-dioxide, 323 mg of (R)-3-methylpiperidinium (R)-mandelate, 0.60 ml of diisopropylethylamine, and 10 ml of acetonitrile was stirred at 70° C. for 2 hours. To the reaction mixture was added 20 ml of water, the mixture was extracted with 20 ml of EtOAc. The organic phase obtained was washed with brine and dried over anhydrous magnesium sulfate, and the solvent was distilled off under reduced pressure. The residue obtained was purified by silica-gel column chromatography (hexane-EtOAc) to yield 0.40 g of solid. To this solid were added 4 ml of EtOH, 8 ml of EtOAc, and 0.5 ml of 4M HCl-EtOAc solution in turn, and the mixture was stirred at ambient temperature. The solvent was distilled off under reduced pressure, and 4 ml of EtOAc was added to the residue to precipitate white solid, which was collected by filtration to yield 188 mg of (R)-2-(4-chloro-2,5-difluorophenyl)-4-(3-methylpiperidin-1-yl)-5,7-dihydrothieno[3,4-d ]pyrimidine 6,6-dioxide hydrochloride.

Example 2

A mixture of 37.04 g ethyl 4-{1-[2-(4-chloro-2,5-difluorophenyl)-6,7-dihydro-5H-cyclopenta[d]pyrimidin-4-yl]piperidin-4-yl}butanoate, 160 ml of 1M aqueous sodium hydroxide, and 400 ml of THF-EtOH (1:1) was stirred at ambient temperature for 4 hours. To the reaction mixture, 160 ml of 1M hydrochloric acid aqueous solution and 700 ml of water were added, and the mixture was extracted twice with chloroform. The organic phase obtained was dried over anhydrous magnesium sulfate, and the solvent was distilled off under reduced pressure. The solid obtained was dissolved in 300 ml of THF, 50 ml of 4M HCl-EtOAc solution was added, the solution was concentrated under reduced pressure, and the resultant solid was recrystallized from water-acetonitrile to yield 25.35 g of 4-{1-[2-(4-chloro-2,5-difluorophenyl)-6,7-dihydro-5H-cyclopenta[d]pyrimidin-4-yl]piperidin-4-yl}butanoic acid hydrochloride.

Example 3

A mixture of 390 mg of ethyl {1-[2-(4-chloro-2,5-difluorophenyl)-6,6-dioxo-5,7-dihydrothieno[3,4-d]pyrimidin-4-yl]piperidin-4-ylidene}acetate, 10 ml of 6M hydrochloric acid aqueous solution, and 10 ml of THF was stirred at 90° C. for 5.5 hours. The solvent was distilled off under reduced pressure, and the resultant solid was recrystallized from water-acetonitrile to yield 126 mg of {1-[2-(4-chloro-2,5-difluorophenyl)-6,6-dioxo-5,7-dihydrothieno[3,4-d]pyrimidin-4-yl]piperidin-4-ylidene}acetic acid hydrochloride.

Example 4

A mixture of 503 mg of 1-tert-butoxycarbonyl-4-[2-(4-chloro-2,5-difluorophenyl)-5,7-dihydrothieno[3,4-d]pyrimidin-4-yl]piperazine, 2 ml of MeOH, and 6 ml of 4M HCl-dioxane solution was stirred at ambient temperature for 1 hour. To the reaction mixture were added 15 ml of 1M aqueous sodium hydroxide and 2 ml of diethyl ether, and the precipitate was collected by filtration, washed with water and then diethyl ether, and dried under reduced pressure. The solid obtained was dissolved in 5 ml of MeOH, here was added 2 ml of 4M HCl-dioxane solution, and the solvent was then distilled off under reduced pressure. The residue obtained was washed with EtOH-EtOAc and dried under reduced pressure to yield 423 mg of 2-(4-chloro-2,5-difluorophenyl)-4-piperazin-1-yl-5,7-dihydrothieno[3,4-d]pyrimidine dihydrochloride.

Example 5

A mixture of 350 mg of 2-(4-chloro-2,5-difluorophenyl)-4-(piperazin-1-yl)-5,7-dihydrothieno[3,4-d]pyrimidine dihydrochloride, 72 mg of hydroxyacetic acid, 0.22 ml of triethylamine, 128 mg of HOBt, 182 mg of EDCI, and 10 ml of DMF was stirred at ambient temperature for 17 hours. To the reaction mixture 100 ml of water was added, and the precipitate was collected by filtration, washed with water, and dried under reduced pressure at 50° C. The solid obtained was dissolved in 15 ml of THF, here was added 2 ml of 4M HCl-dioxane solution, and the solution was concentrated under reduced pressure to yield solid, which was recrystallized from acetonitrile-ether to yield 315 mg of 2-{4-[2-(4-chloro-2,5-difluorophenyl)-5,7-dihydrothieno[3,4-d]pyrimidin-4-yl]piperazin-1-yl}-2-oxoethanol hydrochloride.

Example 6

To a mixture of 364 mg of 2-(4-chloro-2,5-difluorophenyl)-4-(piperazin-1-yl)-5,7-dihydrothieno[3,4-d]pyrimidine dihydrochloride, 0.71 ml of diisopropylethylamine, and 10 ml of DMF, 0.08 ml of methanesulfonyl chloride was added, and the resultant mixture was stirred at ambient temperature for 19 hours. To the reaction mixture was added 100 ml of water, the precipitate was collected by filtration, washed with water, and dried under reduced pressure at 50° C. to yield 329 mg of faint brown solid. This solid was dissolved in 15 ml of THF, here was added 2 ml of 4M HCl-dioxane solution, and the solvent was distilled off under reduced pressure, the resultant residue was recrystallized from acetonitrile-water-ether to yield 314 mg of 2-(4-chloro-2,5-difluorophenyl)-4-[4-(methylsulfonyl)piperazin-1-yl]-5,7-dihydrothieno[3,4-d]pyrimidine hydrochloride.

Example 7

A mixture of 246 mg of [1-(2-cyclopentyl-6,6-dioxo-5,7-dihydrothieno[3,4-d]pyrimidin-4-yl)piperidin-4-yl]acetic acid, 75 mg of ammonium carbonate, 0.11 g of HOBt, 0.16 g of EDCI, and 6 ml of DMF was stirred at ambient temperature for 3 days. The solvent was distilled off under reduced pressure, water was added to the residue, and the mixture was extracted with EtOAc. The organic phase obtained was washed with a saturated aqueous sodium bicarbonate and brine and dried over anhydrous magnesium sulfate, and the solvent was distilled off under reduced pressure. The residue obtained was purified by silica-gel column chromatography (chloroform-MeOH) to yield a foamy product. This product was dissolved in THF, here was added 4M HCl-dioxane solution, the solution was concentrated under reduced pressure, the residue was washed with ether to yield 184 mg of [1-(2-cyclopentyl-6,6-dioxo-5,7-dihydrothieno[3,4-d]pyrimidin-4-yl)piperidin-4-yl]acetamide hydrochloride.

Example 8

To a mixture of 500 mg of 1-[6,6-dioxido-2-(2,4,5-trifluorophenyl)-5,7-dihydrothieno[3,4-d]pyrimidin-4-yl]-1,4-diazepan-5-one and 5 ml of DMSO, 89 mg of sodium thiomethoxide was added, the mixture was stirred at ambient temperature for 1 hour, here was then added 21 mg of sodium thiomethoxide, and the mixture was stirred at ambient temperature for 30 minutes. To the reaction mixture was added 50 ml of water, and the precipitate was collected by filtration, washed with water, and dried under reduced pressure. The filtrate was separately extracted with a mixture of EtOAc and THF, the organic phase obtained was dried over anhydrous magnesium sulfate, the solvent was distilled off under reduced pressure, and the solid obtained was combined with the former solid. The mixture was purified by silica-gel column chromatography (chloroform-MeOH) to yield 352 mg of 1-{2-[2,5-difluoro-4-(methylthio)phenyl]-6,6-dioxido-5,7-dihydrothieno[3,4-d]pyrimidin-4-yl}-1,4-diazepan-5-one.

Example 9

To a mixture of 300 mg of 1-[6,6-dioxido-2-(2,4,5-trifluorophenyl)-5,7-dihydrothieno[3,4-d]pyrimidin-4-yl]-1,4-diazepan-5-one and 6 ml of DMSO, 95 mg of potassium cyanide and 383 mg of 18-crown-6-ether were added, and the mixture was stirred at ambient temperature for 1 hour and then at 80° C. for 1.5 hour. To the reaction mixture was added 30 ml of water, the product was extracted with EtOAc-THF mixed solvent. The organic phase obtained was washed with brine, dried over anhydrous magnesium sulfate, and evaporated under reduced pressure. The residue obtained was purified by silica-gel column chromatography (chloroform-MeOH) to yield 49 mg of solid, which was washed with acetonitrile-diethyl ether to yield 39 mg of 4-[6,6-dioxido-4-(5-oxo-1,4-diazepan-1-yl)-5,7-dihydrothieno[3,4-d]pyrimidin-2-yl]-2,5-difluorobenzonitrile.

Example 10

To a mixture of 547 mg of ethyl 3-{1-[2-(4-chloro-2,5-difluorophenyl)-6,6-dioxido-5,7-dihydrothieno[3,4-d]pyrimidin-4-yl]piperidin-4-yl}propionate, 5 ml of THF, and 5 ml of ethanol, was added 59 mg of lithium borohydride with ice-cooling, the resultant mixture was stirred at ambient temperature for 18 hours and then at 60° C. for 3 days. To this mixture was added dropwise 20 ml of 1M hydrochloric acid aqueous solution with ice-cooling, the resultant mixture was stirred at ambient temperature for 10 minutes, and then 50 ml of 1M aqueous sodium hydroxide was added. The precipitate was collected by filtration, washed with water, dried under reduced pressure, and purified by silica-gel column chromatography (chloroform-MeOH) to yield 280 mg of solid. This solid was dissolved in THF, here was added 4M HCl-dioxane solution, the solution was concentrated under reduced pressure, and the resultant residue was recrystallized from acetonitrile-diethyl ether to yield 256 mg of 3-{1-[2-(4-chloro-2,5-difluorophenyl)-6,6-dioxido-5,7-dihydrothieno[3,4-d]pyrimidin-4-yl}piperidin-4-yl}propan-1-ol hydrochloride.

Example 11

A mixture of 400 mg of 1-[2-(4-chloro-2,5-difluorophenyl)-6,6-dioxido-5,7-dihydrothieno[3,4-d]pyrimidin-4-yl]piperidin-4-one, 10 ml of methylene chloride, 65 µl of aminoethanol, and two drops of acetic acid was stirred at ambient temperature for 1 hour, here was then added 617 mg of sodium triacetoxyborohydride, and the mixture was stirred at ambient temperature for 3 hours. Saturated aqueous sodium bicarbonate was added to the reaction mixture, and the resultant mixture was extracted with chloroform-THF mixed solvent. The organic phase obtained was washed with brine and dried over anhydrous magnesium sulfate, and the solvent was distilled off under reduced pressure. The residue obtained was dissolved in THF-MeOH, here was added 4M HCl-dioxane solution, the solution was concentrated under reduced pressure, and the residue was recrystallized from EtOH-acetonitrile to yield 426 mg of 2-({1-[2-(4-chloro-2,5-difluorophenyl)-6,6-dioxido-5,7-dihydrothieno[3,4-d]pyrimidin-4-yl]piperidin-4-yl}amino)ethanol dihydrochloride.

Example 12

To a mixture of 200 mg of 8-[2-(4-chloro-2,5-difluorophenyl)-6,6-dioxido-5,7-dihydrothieno[3,4-d]pyrimidin-4-yl]-2,8-diazaspiro[4.5]decane dihydrochloride and 10 ml of acetonitrile, were added 263 mg of potassium carbonate, 6 mg of potassium iodide, and 89 µl of (2-bromoethoxy)(tert-butyl)dimethylsilane, and the mixture was stirred at 60° C. for 3 days. Water was added to the mixture, and the resultant mixture was extracted with EtOAc. The organic phase obtained was washed with 10% aqueous citric acid, brine, saturated aqueous sodium bicarbonate, and brine in turn and dried over anhydrous magnesium sulfate, and the solvent was distilled off under reduced pressure. The residue obtained was purified by silica-gel column chromatography (chloroform-methanol) to yield 199 mg of solid. To this solid were added 5 ml of 4M HCl-dioxane a solution and 2 ml of methanol, the mixture was stirred at ambient temperature for 1 hour and then concentrated under reduced pressure, and the residue was recrystallized from EtOH-acetonitrile-diethyl ether to yield 169 mg of 2-{8-[2-(4-chloro-2,5-difluorophenyl)-6,6-dioxido-5,7-dihydrothieno[3,4-d]pyrimidin-4-yl]-2,8-diazaspiro[4.5]decan-2-yl}ethanol dihydrochloride.

Example 13

To a mixture of 200 mg of (2Z)-3-{1-[2-(4-chloro-2,5-difluorophenyl)-6,6-dioxido-5,7-dihydrothieno[3,4-d]pyrimidin-4-yl]piperidin-4-yl}acrylic acid, 5 ml of THF, and 47 µl of 4-methylmorpholine, 1 ml of a THF solution containing 56 µl of isobutyl chloroformate was added dropwise at −10 to −15° C., the mixture was stirred at this temperature for 50 minutes, then here was added 25 mg of sodium borohydride, and the mixture was stirred at ambient temperature for 30 minutes. To the reaction mixture was added 3 ml of ethanol, and the resultant mixture was stirred at ambient temperature for 30 minutes, then water and 1M hydrochloric acid aqueous solution were added, and the mixture was stirred for 15 minutes. The reaction mixture was made alkaline by adding 1M aqueous sodium hydroxide aqueous solution and then extracted with EtOAc. The organic phase obtained was dried over anhydrous magnesium sulfate, and the solvent was distilled off under reduced pressure. The residue obtained was purified by silica-gel column chromatography (chloroform-MeOH) to yield 108 mg of solid. This solid was dissolved in THF, here was added 4M HCl-dioxane solution, the solution was concentrated under reduced pressure, and the residue was recrystallized from acetonitrile-diethyl ether to yield 62 mg of (2Z)-3-{1-[2-(4-chloro-2,5-difluorophenyl)-6,6-dioxido-5,7-dihydrothieno[3,4-d]pyrimidin-4-yl]piperidin-4-yl}prop-2-en-1-ol hydrochloride.

Example 14

A mixture of 264 mg of 2-(4-chloro-2,5-difluorophenyl)-4-(2,3,6,7-tetrahydro-1H-azepin-1-yl)-5,7-dihydrothieno[3,4-d]pyrimidine 6,6-dioxide, a few drops of 2.5-wt % tert-BuOH solution of osmium tetraoxide, 75 mg of N-methylmorpholine-N-oxide, 6 ml of THF, and 3 ml of water was stirred at ambient temperature for 4.5 hours. Aqueous sodium thiosulfate solution was added to the reaction mixture, and the precipitate was collected by filtration, washed with 50 ml of water and 50 ml of EtOAc-hexane (1:1), and dried under reduced pressure at 70° C. to yield 244 mg of colorless solid. This solid was dissolved in THF, here was added 4M HCl-dioxane solution, the solvent was distilled off under reduced pressure, and the residue was washed with EtOH to yield 264 mg of (4R,5S)-1-[2-(4-chloro-2,5-difluorophenyl)-6,6-dioxido-5,7-dihydrothieno[3,4-d]pyrimidin-4-yl]azepan-4,5-diol hydrochloride.

Example 15

A mixture of 321 mg of 1-[2-(4-chloro-2,5-difluorophenyl)-6,6-dioxido-5,7-dihydrothieno[3,4-d]pyrimidin-4-yl]-1,4-diazepan-5-one and 10 ml of 5% sulfuric acid was stirred at 100° C. for 27 hours. After the solvent was distilled off under reduced pressure, 10 ml of dioxane, 10 ml of saturated aqueous sodium bicarbonate solution, and 0.18 g of DIBOC (tert-butoxycarbonyl anhydride) were added in turn to the residue obtained, and the mixture was stirred at ambient temperature for 1 hour. Precipitate was filtered, and the filtrate was evaporated under reduced pressure. The residue was dissolved in chloroform, washed with 5% aqueous citric acid solution and then water, and dried over anhydrous magnesium sulfate. The solvent was distilled off under reduced pressure, and 4M HCl-dioxane solution was added to the residue, the resultant solution was stirred, and then the solvent was distilled off under reduced pressure. To the residue was added saturated aqueous sodium bicarbonate solution, the aqueous solution was washed with chloroform, added 5% aqueous citric acid, and extracted with chloroform. The organic extract was washed with water, and the solvent was distilled off under reduced pressure. The residue was dissolved in THF, here was added 4M HCl-dioxane solution, precipitate was collected by filtration to yield 92 mg of N-(2-aminoethyl)-N-[2-(4-chloro-2,5-difluorophenyl)-6,6-dioxido-5,7-dihydrothieno[3,4-d]pyrimidin-4-yl]-β-alanine dihydrochloride as colorless solid.

Example 16

A mixture of 2.20 g of 2-{1-[2-(4-chloro-2,5-difluorophenyl)-6,6-dioxido-5,7-dihydrothieno[3,4-d]pyrimidin-4-yl]piperidin-4-yl}acetamide and 20 ml of phosphorous oxychloride was stirred at 100° C. for 30 minutes. Excess phosphorous oxychloride was distilled off under reduced pressure, saturated aqueous sodium bicarbonate solution and EtOAc were added to the residue. Precipitate was collected by filtration, washed with water and EtOAc, and dried under reduced pressure at 70° C. to yield 1.69 g of faint brown solid. This solid was dissolved in THF-MeOH, here was added 4M HCl-dioxane solution, the solvent was distilled off under reduced pressure, and the residue was washed with acetonitrile to yield 81 mg of {1-[2-chloro-2,5-difluorophenyl]-6,6-dioxido-5,7-dihydrothieno[3,4-d]pyrimidin-4-yl}piperidin-4-yl}acetonitrile hydrochloride as colorless solid.

Example 17

A mixture of 571 mg of 1-[2-(4-chloro-2,5-difluorophenyl)-6,6-dioxido-5,7-dihydrothieno[3,4-d]pyrimidin-4-yl]piperidin-4-ol, 0.30 g of 4-nitrophenyl chloroformate, 0.12 ml of pyridine, and 10 ml of methylene chloride was stirred at ambient temperature for 17 hours. Saturated aqueous ammonium chloride solution was added to the reaction mixture, and the mixture was extracted twice with chloroform. The organic phase was washed with brine, dried over anhydrous magnesium sulfate, and evaporated under reduced pressure to yield 894 mg of 1-[2-(4-chloro-2,5-difluorophenyl)-6,6-dioxido-5,7-dihydrothieno[3,4-d]pyrimidin-4-yl]piperidin-4-yl 4-nitrophenyl carbonate as light yellow solid.

A mixture of 300 mg of 1-[2-(4-chloro-2,5-difluorophenyl)-6,6-dioxido-5,7-dihydrothieno[3,4-d]pyrimidin-4-yl]piperidin-4-yl 4-nitrophenyl carbonate, 43 mg of 2-(methylamino)ethanol, and 5 ml of DMF was stirred at ambient temperature for 19.5 hours. Saturated aqueous sodium bicarbonate solution was added to the reaction mixture, the mixture was extracted twice with chloroform. The organic phase was washed with brine, dried over anhydrous magnesium sulfate, and evaporated under reduced pressure. The yellow oil obtained was dissolved in THF, here was added 4M HCl-dioxane solution, and the solution was concentrated under reduced pressure to give solid, which was recrystallized from acetonitrile-ether to yield 120 mg of 1-[2-(4-chloro-2,5-difluorophenyl)-6,6-dioxido-5,7-dihydrothieno[3,4-d]pyrimidin-4-yl]piperidin-4-yl (2-hydroxyethyl)methylcarbamate hydrochloride as colorless solid.

Example 18

A mixture of 230 mg of 1-[2-(4-chloro-2,5-difluorophenyl)-6,6-dioxido-5,7-dihydrothieno[3,4-d]pyrimidin-4-yl]piperidin-4-one, 140 mg of ethyl 4-aminobutyrate hydrochloride, 0.1 ml of acetic acid, 5 ml of dichloroethane, and 5 ml of DMF was stirred at ambient temperature for 1 hour, here was then added 353 mg of sodium triacetoxyborohydride, and the mixture was stirred at ambient temperature for 19 hours. Saturated aqueous sodium bicarbonate solution was added to the reaction mixture, the mixture was extracted twice with chloroform, the organic phase was washed with brine and dried over anhydrous magnesium sulfate, and the solvent was distilled off under reduced pressure. The residue obtained was purified by silica-gel column chromatography (chloroform-MeOH) to yield 128 mg of ethyl 4-({1-[2-(4-chloro-2,5-difluorophenyl)-6,6-dioxido-5,7-dihydrothieno[3,4-d]pyrimidin-4-yl]piperidin-4-yl}amino)butanoate and 91 mg of 1-{1-[2-(4-chloro-2,5-difluorophenyl)-6,6-dioxido-5,7-dihydrothieno[3,4-d]pyrimidin-4-yl]piperidin-4-yl}pyrrolidin-2-one. Recrystallization of the latter from EtOH gave 65 mg of 1-{1-[2-(4-chloro-2,5-difluorophenyl)-6,6-dioxido-5,7-dihydrothieno[3,4-d]pyrimidin-4-yl]piperidin-4-yl}pyrrolidin-2-one as colorless solid.

Example 19

A mixture of 254 mg of 2-{1-[2-(4-chloro-2,5-difluorophenyl)-6,6-dioxido-5,7-dihydrothieno[3,4-d]pyrimidin-4-yl]piperidin-4-yl}amino)ethanol, 103 mg of NaOMe, 0.2 ml of diethyl carbonate, and 5 ml of MeOH was stirred at 70° C. for 46 hours. Water was added to the reaction mixture, and precipitate was collected by filtration, washed with water, and dried under reduced pressure at 70° C. to yield 193 mg of solid. The solid obtained was dissolved in THF-MeOH, here was added 4M HCl-dioxane solution, and the solution was concentrated under reduced pressure. Recrystallization of the resultant solid from EtOH-acetonitrile-ether gave 172 mg of 3-{1-[2-(4-chloro-2,5-difluorophenyl)-6,6-dioxido-5,7-dihydrothieno[3,4-d]pyrimidin-4-yl]piperidin-4-yl}-1,3-oxazolidin-2-one hydrochloride as light yellow solid.

Example 20

A mixture of 208 mg of 2-(4-chloro-2,5-difluorophenyl)-4-piperazin-1-yl-5,7-dihydrothieno[3,4-d]pyrimidine 6,6-dioxide dihydrochloride, 0.19 ml of diisopropylethylamine, 0.1 ml of ethyl isocyanate, and 5 ml of DMF was stirred at ambient temperature for 1 hour. Water was added to the reaction mixture, and precipitate was collected by filtration, washed with water, and dried under reduced pressure at 70° C. to yield 193 mg of colorless solid. The solid obtained was dissolved in THF, here was added 4M HCl-dioxane solution, and the solution was concentrated under reduced pressure to yield solid, which was recrystallized from EtOH-acetonitrile to yield 159 mg of 4-[2-(4-chloro-2,5-difluorophenyl)-6,6-dioxido-5,7-dihydrothieno[3,4-d]pyrimidin-4-yl]-N-ethylpiperazine-1-carboxamide hydrochloride as colorless solid.

Example 21

In 5 ml of methylene chloride was dissolved 180 mg of trans-4-{[2-(4-chloro-2,5-difluorophenyl)-6,6-dioxido-5,7-dihydrothieno[3,4-d]pyrimidin-4-yl]amino}cyclohexanol, here was added 0.11 ml of DAST ((diethylamino)sulfur trifluoride) at −78° C., and the mixture was stirred for 3 hours. Saturated aqueous sodium bicarbonate solution was added to the reaction mixture, and the mixture was extracted twice with chloroform. The organic phase was washed with brine, dried over anhydrous magnesium sulfate, and evaporated under reduced pressure. The residue obtained was purified by silica-gel column chromatography (hexane-EtOAc) to yield 137 mg of colorless solid. This solid was dissolved in THF, here was added 4M HCl-dioxane solution, the solution was concentrated under reduced pressure, and the residue was washed with EtOH to yield 83 mg of 2-(4-chloro-2,5-difluorophenyl)-N-cyclohex-3-en-1-yl-5,7-dihydrothieno[3,4-d]pyrimidine-4-amine 6,6-dioxide hydrochloride as colorless solid.

Example 22

A mixture of 600 mg of 4-chloro-2-(4-chloro-2,5-difluorophenyl)-5,7-dihydrothieno[3,4-d]pyrimidine 6,6-dioxide, 367 mg of 4-(3-hydroxypropyl)piperidin-4-ol hydrochloride, 0.90 ml of diisopropylethylamine, and 10 ml of acetonitrile was stirred at 70° C. for 12 hours. To the reaction mixture, 20 ml of water was added, and the mixture was extracted with 30 ml of chloroform. The organic phase obtained was washed with brine and dried over anhydrous magnesium sulfate, and the solvent was distilled off under reduced pressure. To the residue obtained were added in turn 10 ml of EtOH and 2 ml of 4M HCl-dioxane solution, the solvent was distilled off under reduced pressure, EtOH and EtOAc were added to the residue, the resultant mixture was heated with stirring and then allowed to cool, and precipitate was separated by filtration. To the filtrate was added triethylamine, the solvent was distilled off under reduced pressure, and the residue was purified by silica-gel column chromatography (chloroform-MeOH) to yield 120 mg of an oil. To this oil were added in turn 10 ml of THF and 0.5 ml of 4M HCl-dioxane solution, and the solvent was distilled off under reduced pressure. The residue obtained was recrystallized from THF-diethyl ether to yield 64 mg of 3-{1-[2-(4-chloro-2,5-difluorophenyl)-6,6-dioxido-5,7-dihydrothieno[3,4-d]pyrimidin-4-yl]-4-hydroxypiperidin-4-yl}propyl acetate hydrochloride.

The compounds given in Tables 10 to 31 below were prepared using the above methods, methods obvious to those skilled in the art, or modified methods thereof. Chemical structures and spectral data of these compounds in Examples are shown in Tables. Symbols in Tables have the following meanings (ditto hereinafter). Ex: Example number (a line wherein only a numeral is given in the column of Ex means that the compound in said Example number is hydrochloride, whereas a line wherein a numeral is followed by slash (/) and "f" means that the compound in said Example number is a free form.)

TABLE 10

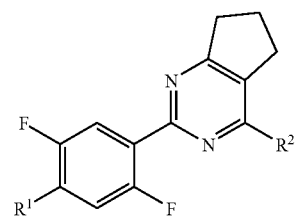

| Ex | R¹ | R² | Data |
|---|---|---|---|
| 2 | Cl | 4-(HO₂C(CH₂)₃)-pipe | MS: 436 |
| 23 | F | 4-(HO₂CCH₂)-pipe | MS: 392 |
| 24/f | F | 4-(EtO₂CCH₂)-pipe | |
| 25 | F | 4-(HO₂C(CH₂)₂)-pipe | MS: 406 |
| 26/f | F | 4-(EtO₂C(CH₂)₂)-pipe | |
| 27 | F | 4-(HO₂C(CH₂)₃)-pipe | MS: 420 |
| 28/f | F | 4-(EtO₂C(CH₂)₃)-pipe | |
| 29 | F | (S)-3-(HO₂CCH₂)-pipe | MS: 392 |
| 30/f | F | (S)-3-(EtO₂CCH₂)-pipe | |
| 31 | F | (S)-3-(HO₂C(CH₂)₂)-pipe | MS: 406 |
| 32/f | F | (S)-3-(EtO₂C(CH₂)₂)-pipe | |
| 33 | F | 4-(HO₂CCH₂)-hPy | MS: 390 |
| 34/f | F | 4-(EtO₂CCH₂)-hPy | |
| 35 | Cl | 4-(EtO₂C)-azep | MS: 436 |
| 36 | Cl | 4-(HO₂C)-azep | MS: 408 |
| 37 | Cl | (S)-3-(HO₂C(CH₂)₂)-pipe | MS: 422 |
| 38/f | Cl | (S)-3-(EtO₂C(CH₂)₂)-pipe | MS: 450 |
| 39 | Cl | (R)-3-(HO₂C(CH₂)₂)-pipe | MS: 422 |
| 40/f | Cl | (R)-3-(EtO₂C(CH₂)₂)-pipe | MS: 450 |

TABLE 10-continued

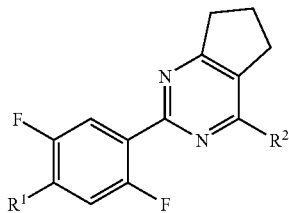

| Ex | R¹ | R² | Data |
|----|----|----|------|
| 41 | Cl | 4-(HOCH$_2$CO)-pipa | MS: 409 |
| 42 | Cl | 4-Ms-pipa | MS: 429 |
| 43 | Cl | 2-(HO$_2$CCH$_2$)-mor | MS: 410 |
| 44/f | Cl | 2-(EtO$_2$CCH$_2$)-mor | |
| 45 | Cl | 3-(HO$_2$CCH$_2$)-pipa | MS: 409 |
| 46/f | Cl | 3-(MeO$_2$CCH$_2$)-pipa | |
| 47 | Cl | 3-(HO$_2$C(CH$_2$)$_2$)-pipe | MS: 422 |
| 48/f | Cl | 3-(MeO$_2$C(CH$_2$)$_2$)-pipe | |
| 49 | Cl | mor | MS: 352 |
| 50 | Cl | pipe | MS: 350 |

TABLE 11

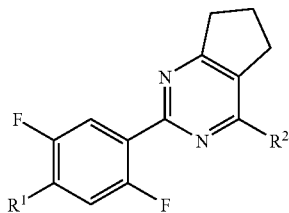

| Ex | R¹ | R² | Data |
|----|----|----|------|
| 51 | Cl | azep | MS: 364 |
| 52/f | Cl | 4-Me-pipe | MS: 364 |
| 53/f | Cl | 4-(EtO$_2$C)-pipe | MS: 422 |
| 54 | Cl | 4-(HO$_2$C)-pipe | MS: 394 |
| 55 | Cl | 4-(HOCH$_2$)-pipe | MS: 380 |
| 56 | Cl | 4-(HO(CH$_2$)$_2$)-pipe | MS: 394 |
| 57 | Cl | 4-Ac-pipa | MS: 393 |
| 58 | Cl | 4-(HO(CH$_2$)$_2$)-pipa | MS: 395 |
| 59 | Cl | 4-(HO$_2$C(CH$_2$)$_2$)-pipe | MS: 422 |
| 60 | Cl | 1,4-dioxa-8-azaspiro[4.5]decan-8-yl | MS: 408 |
| 61 | Cl | pipa | MS: 351 |
| 62/f | Cl | 4-Boc-pipa | MS: 451 |
| 63 | Cl | hpipa | MS: 365 |
| 64/f | Cl | 4-Boc-hpipa | MS: 465 |
| 65 | Cl | azocan-1-yl | MS: 378 |
| 66 | Cl | 4-(EtO$_2$CCH$_2$)-pipe | MS: 436 |
| 67 | Cl | 4-(H$_2$NCO)-pipe | MS: 393 |
| 68 | Cl | 3-Me-pipe | MS: 364 |
| 69 | Cl | 4-(HO$_2$CCH$_2$)-pipe | MS: 408 |
| 70 | Cl | 5-oxo-hpipa | MS: 379 |
| 71 | Cl | (R)-3-(HO$_2$CCH$_2$)-pipe | MS: 408 |
| 72/f | Cl | (R)-3-(EtO$_2$CCH$_2$)-pipe | MS: 436 |
| 73 | Cl | (S)-3-(HO$_2$CCH$_2$)-pipe | MS: 408 |
| 74/f | Cl | (S)-3-(EtO$_2$CCH$_2$)-pipe | MS: 436 |
| 75 | Cl | 3-(HO$_2$CCH$_2$)-pipe | MS: 408 |
| 76/f | Cl | 3-(EtO$_2$CCH$_2$)-pipe | MS: 436 |
| 77 | Cl | 4-(HO$_2$CCH$_2$)-hPy | MS: 406 |
| 78/f | Cl | 4-(EtO$_2$CCH$_2$)-hPy | MS: 434 |
| 79 | Cl | (Z)-4-(carboxymethylene)-pipe | MS: 406 |

TABLE 12

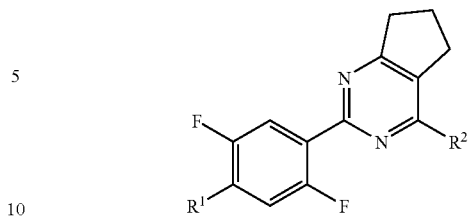

| Ex | R¹ | R² | Data |
|----|----|----|------|
| 80/f | Cl | (Z)-4-(ethoxycarbonylmethylene)-pipe | MS: 434 |
| 81/f | Cl | 4-(F$_2$HCCO)-pipa | ME: 429 |
| 82/f | Cl | 4-(2-fur-CO)-pipa | ME: 445 |
| 83/f | Cl | 4-((HO)(Et)(Me)CCO))-pipa | ME: 451 |
| 84/f | Cl | 4-(HO(CH$_2$)$_2$CO)-pipa | ME: 423 |
| 85/f | Cl | 4-(HOCH(Me)CH$_2$CO)-pipa | ME: 437 |
| 86/f | Cl | 4-(5-OHC-2-fur-CO)-pipa | ME: 473 |
| 87/f | Cl | 4-(HOCH$_2$C(Me)$_2$CO)-pipa | ME: 451 |
| 88/f | Cl | 4-(EtOCH$_2$CO)-pipa | ME: 437 |
| 89/f | Cl | 4-((HOCH$_2$)$_2$C(Me)CO)-pipa | ME: 467 |
| 90/f | Cl | 4-(CH$_3$CO(CH$_2$)$_2$CO)-pipa | ME: 449 |
| 91/f | Cl | 4-(3-oxo-cPen-CO)-pipa | ME: 461 |
| 92/f | Cl | 4-(tetrahydrofuran-3-yl-CO)-pipa | ME: 449 |
| 93/f | Cl | 4-(EtO$_2$CCH$_2$CO)-pipa | ME: 465 |
| 94/f | Cl | 4-(3-oxo-cHex-CO)-pipa | ME: 475 |
| 95/f | Cl | 4-((5-oxopyrrolidin-2-yl)SCH$_2$CO)-pipa | ME: 508 |
| 96/f | Cl | 4-(cyclopenten-4-yl-CO)-pipa | ME: 445 |
| 97/f | Cl | 4-(2-fur-CONHCH$_2$CO)-pipa | ME: 502 |
| 98/f | Cl | 4-(EtO$_2$C(CH$_2$)$_3$CO)-pipa | ME: 493 |
| 99/f | Cl | 4-((2,5-dioxoimidazolidin-4-yl)CH$_2$CO)-pipa | ME: 491 |
| 100/f | Cl | 4-(3-H$_2$N-pyrazin-2-yl-CO)-pipa | ME: 472 |
| 101/f | Cl | 4-(2-HO$_2$C-cPen-CO)-pipa | ME: 491 |
| 102/f | Cl | 4-(2-HO$_2$C-cHex-CO)-pipa | ME: 505 |
| 103/f | Cl | 4-(5-HO$_2$C-2-fur-CH$_2$NH)-pipe | ME: 489 |
| 104/f | Cl | 4-(3,5-diOH-Ph-CH$_2$NH)-pipe | ME: 487 |
| 105/f | Cl | 4-(2-HO$_2$C-Ph-CH$_2$NH)-pipe | ME: 499 |

TABLE 13

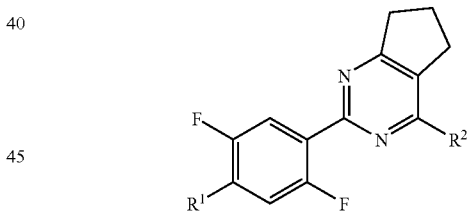

| Ex | R¹ | R² | Data |
|----|----|----|------|
| 106/f | Cl | 4-(2-HO-3-MeO—Ph—CH$_2$NH)-pipe | ME: 501 |
| 107/f | Cl | 4-(5-O$_2$N-2-fur-CH$_2$NH)-pipe | ME: 490 |
| 108/f | Cl | 4-(thiazol-2-yl-CH$_2$NH)-pipe | ME: 462 |
| 109/f | Cl | 4-(4-Pyox-CH$_2$NH)-pipe | ME: 472 |
| 110/f | Cl | 4-(quinolin-4-yl-CH$_2$NH)-pipe | ME: 506 |
| 111/f | Cl | 4-(3-HO$_2$C-4,5,6,7-tetrahydrobenzofuran-4-yl-NH)-pipe | ME: 529 |
| 112 | Br | mor | MS: 396 |
| 113 | Br | 4-(HO$_2$CCH$_2$)-pipe | MS: 452 |
| 114/f | Br | 4-(EtO$_2$CCH$_2$)-pipe | |
| 115 | Br | 4-(HO$_2$C(CH$_2$)$_2$)-pipe | MS: 466 |
| 116/f | Br | 4-(EtO$_2$C(CH$_2$)$_2$)-pipe | |
| 117 | Br | 4-(HO$_2$C(CH$_2$)$_3$)-pipe | MS: 480 |
| 118/f | Br | 4-(EtO$_2$C(CH$_2$)$_3$)-pipe | |
| 119 | Br | (S)-3-(HO$_2$C(CH$_2$)$_2$)-pipe | MS: 466 |
| 120/f | Br | (S)-3-(EtO$_2$C(CH$_2$)$_2$)-pipe | |
| 121 | Br | 4-(HO$_2$CCH$_2$)-hPy | MS: 450 |
| 122/f | Br | 4-(EtO$_2$CCH$_2$)-hPy | |
| 123 | Br | (S)-3-(HO$_2$CCH$_2$)-pipe | MS: 452 |
| 124/f | Br | (S)-3-(EtOphd 2CCH$_2$)-pipe | |

TABLE 14

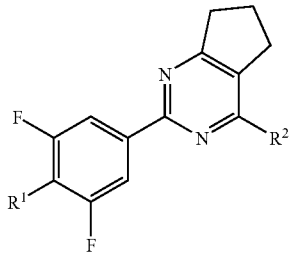

| Ex | R¹ | R² | Data |
|---|---|---|---|
| 125 | F | 4-(HO₂CCH₂)-pipe | MS: 392 |
| 126 | F | 4-(HO₂C(CH₂)₂)-pipe | MS: 406 |
| 127 | F | 4-(HO₂C(CH₂)₃)-pipe | MS: 420 |
| 128 | F | (S)-3-(HO₂CCH₂)-pipe | MS: 392 |
| 129 | F | 4-(HO₂CCH₂)-hPy | MS: 390 |
| 130 | F | (S)-3-(HO₂C(CH₂)₂)-pipe | MS: 406 |
| 131 | Cl | 4-(HO₂CCH₂)-pipe | MS: 408 |
| 132 | Cl | 4-(HO₂C(CH₂)₂)-pipe | MS: 422 |
| 133 | Cl | 4-(HO₂C(CH₂)₃)-pipe | MS: 436 |
| 134 | Cl | (S)-3-(HO₂CCH₂)-pipe | MS: 408 |
| 135 | Cl | (S)-3-(HO₂C(CH₂)₂)-pipe | MS: 422 |
| 136 | Cl | 4-(HO₂CCH₂)-hPy | MS: 406 |
| 137 | Br | 4-(HO₂CCH₂)-pipe | ME: 452 |
| 138/f | Br | 4-(EtO₂CCH₂)-pipe | MS: 480 |
| 139 | Br | 4(HO₂C(CH₂)₂)-pipe | ME: 466 |
| 140/f | Br | 4-(EtO₂C(CH₂)₂)-pipe | MS: 494 |
| 141 | Br | 4-(HO₂C(CH₂)₃)-pipe | MF: 481 |
| 142/f | Br | 4-(EtO₂C(CH₂)₃)-pipe | MS: 508 |
| 143 | Br | (S)-3-(HO₂CCH₂)-pipe | ME: 452 |
| 144/f | Br | (S)-3-(EtO₂CCH₂)-pipe | MS: 480 |
| 145 | Br | (S)-3-(HO₂C(CH₂)₂)-pipe | ME: 468 |
| 146/f | Br | (S)-3-(EtO₂C(CH₂)₂)-pipe | MS: 494 |
| 147 | Br | 4-(HO₂CCH₂)-hPy | MS: 450 |
| 148/f | Br | 4-(EtO₂CCH₂)-hPy | MS: 478 |

TABLE 15

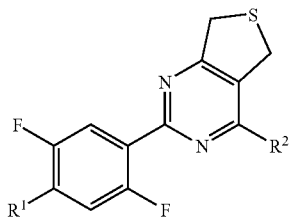

| Ex | R¹ | R² | Data |
|---|---|---|---|
| 4 | Cl | pipa | ME: 369 |
| 5 | Cl | 4-(HOCH₂CO)-pipa | MS: 427 |
| 6 | Cl | 4-Ms-pipa | MS: 447 |
| 149 | F | 4-(HO₂CCH₂)-hPy | MS: 408 |
| 150/f | F | 4-(HO₂CCH₂)-pipe | MS: 410 |
| 151/f | F | 4-(HO₂C(CH₂)₂)-pipe | MS: 424 |
| 152/f | F | 4-(HO₂C(CH₂)₃)-pipe | MS: 438 |
| 153/f | F | (S)-3-(HO₂C(CH₂)₂)-pipe | MS: 424 |
| 154 | F | (S)-3-(HO₂CCH₂)-pipe | MS: 410 |
| 155 | Cl | 4-(HO₂C(CH₂)₂)-pipe | MS: 440 |
| 156 | Cl | 4-(HO₂C(CH₂)₃)-pipe | MS: 454 |
| 157/f | Cl | 4-Boc-pipa | MS: 469 |
| 158 | Cl | hpipa | ME: 383 |
| 159/f | Cl | 4-Boc-hpipa | MS: 483 |
| 160 | Cl | 3-Me-pipe | MS: 382 |
| 161 | Cl | 2,3,6,7-tetrahydro-1H-azepin-1-yl | MS: 380 |
| 162 | Cl | azep | ME: 382 |
| 163 | Cl | 4-(HO₂C)-pipe | MS: 412 |
| 164/f | Cl | 4-(EtO₂C)-pipe | MS: 440 |
| 165 | Cl | 5-oxo-hpipa | MS: 397 |

TABLE 15-continued

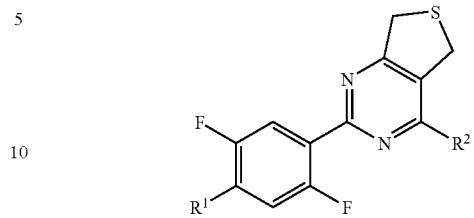

| Ex | R¹ | R² | Data |
|---|---|---|---|
| 166 | Cl | 4-(HO₂CCH₂)-pipe | MS: 426 |
| 167/f | Cl | 4-(EtO₂CCH₂)-pipe | MS: 454 |
| 168 | Cl | pipe | MS: 368 |
| 169 | Cl | mor | MS: 370 |
| 170 | Cl | 4-HO-pipe | MS: 384 |
| 171 | Cl | 3-(HO₂CCH₂)-pipe | MS: 426 |
| 172/f | Cl | 3-(EtO₂CCH₂)-pipe | ME: 454 |
| 173 | Cl | 4-(HO₂C)-azep | MS: 426 |
| 174/f | Cl | 4-(EtO₂C)-azep | MS: 454 |

TABLE 16

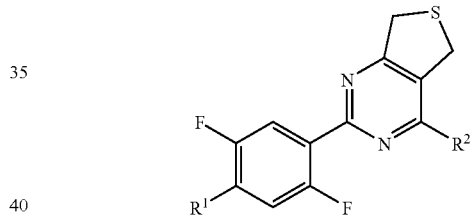

| Ex | R¹ | R² | Data |
|---|---|---|---|
| 175 | Cl | (S)-3-(HO₂C(CH₂)₂)-pipe | MS: 440 |
| 176/f | Cl | (S)-3-(EtO₂C(CH₂)₂)-pipe | MS: 468 |
| 177 | Cl | (R)-3-HO₂C(CH₂)₂-pipe | MS: 440 |
| 178/f | Cl | (R)-3-(EtO₂C(CH₂)₂)-pipe | MN: 466 |
| 179 | Cl | 3-(HO₂CCH₂)-azep | MS: 440 |
| 180/f | Cl | 3-(EtO₂CCH₂)-azep | MS: 468 |
| 181 | Cl | 4-(HO₂CCH₂)-hPy | MS: 424 |
| 182/f | Cl | 4-(EtO₂CCH₂)-hPy | MS: 452 |
| 183 | Cl | (S)-3-(HO₂CCH₂)-pipe | MS: 426 |
| 184/f | Cl | (S)-3-(EtO₂CCH₂)-pipe | MS: 454 |
| 185 | Cl | 2-(HO₂CCH₂)-mor | MS: 428 |
| 186/f | Cl | 2-(EtO₂CCH₂)-mor | |
| 187 | Cl | 4-Ac-pipa | MS: 411 |
| 188 | Cl | 4-(HO(CH₂)₂)-pipa | MS: 413 |
| 189 | Cl | 4-(H₂NOCCH₂)-pipa | MS: 425 |
| 190 | Cl | 4-(MeHNOCCH₂)-pipa | MS: 439 |
| 191 | Cl | 4-(Me₂NOCCH₂)-pipa | MS: 453 |
| 192 | Cl | 4-(HO₂CCH₂)-pipa | MS: 427 |
| 193 | Cl | 4-(H₂NOCCH₂)-pipa | MS: 426 |
| 194 | Cl | 4-(MeHNOCCH₂)-pipa | MS: 440 |
| 195 | Br | 4-(HO₂CCH₂)-hPy | MM: 469 |
| 196/f | Br | 4-(HO₂CCH₂)-pipe | MM: 471 |
| 197/f | Br | 4-(HO₂C(CH₂)₂)-pipe | MM: 485 |
| 198/f | Br | 4-(HO₂C(CH₂)₃)-pipe | MM: 499 |
| 199 | Br | (S)-3-(HO₂CCH₂)-pipe | MS: 471 |
| 200 | Br | (S)-3-(HO₂C(CH₂)₂)-pipe | MM: 485 |

TABLE 17

| Ex | R¹ | R² | Data |
|---|---|---|---|
| 201 | F | 4-(HO₂CCH₂)-pipe | MS: 410 |
| 202 | F | 4-(HO₂C(CH₂)₂)-pipe | MS: 424 |
| 203 | F | 4-(HO₂C(CH₂)₃)-pipe | MS: 438 |
| 204 | F | (S)-3-(HO₂CCH₂)-pipe | MS: 410 |
| 205 | F | (S)-3-(HO₂C(CH₂)₂)-pipe | MS: 424 |
| 206 | F | 4-(HO₂CCH₂)-hPy | MS: 408 |
| 207/f | Cl | 4-(HO₂C(CH₂)₃)-pipe | ME: 454 |
| 208/f | Cl | 4-(EtO₂C(CH₂)₃)-pipe | |
| 209 | Cl | 4-(carboxymethylene)-pipe | MS: 424 |
| 210/f | Cl | 4-(ethoxycarbonylmethylene)-pipe | MS: 452 |
| 211 | Br | 4-(HO₂C(CH₂)₂)-pipe | ME: 498 |
| 212/f | Br | 4-(EtO₂C(CH₂)₃)-pipe | MS: 526 |
| 213 | Br | (S)-3-(HO₂CCH₂)-pipe | ME: 470 |
| 214/f | Br | (S)-3-(EtO₂CCH₂)-pipe | MS: 498 |
| 215 | Br | (S)-3-(HO₂C(CH₂)₂)-pipe | MF: 485 |
| 216/f | Br | (S)-3-(EtO₂C(CH₂)₂)-pipe | MS: 512 |
| 217 | Br | 4-(HO₂CCH₂)-hPy | MS: 468 |
| 218/f | Br | 4-(EtO₂CCH₂)-hPy | MS: 496 |
| 219 | Br | 4-(HO₂CCH₂)-pipe | MS: 470 |
| 220/f | Br | 4-(EtO₂CCH₂)-pipe | MS: 498 |
| 221/f | Br | 4-(HO₂CCH₂)-pipe | ME: 486 |
| 222/f | Br | 4-(EtO₂C(CH₂)₂)-pipe | MS: 512 |

TABLE 18

| Ex | R¹ | R² | Data |
|---|---|---|---|
| 1 | Cl | (R)-3-Me-pipe | MS: 414 |
| 3 | Cl | 4-(carboxymethylene)-pipe | MS: 456 |
| 8/f | MeS— | 5-oxo-hpipa | ME: 441 |
| 9/f | cyano | 5-oxo-hpipa | ME: 420 |
| 10 | Cl | 4-(HO(CH₂)₃)-pipe | MS: 458 |
| 11 | Cl | 4-(HO(CH₂)₂HN)-pipe | MS: 459 |
| 12 | Cl | 2-(HO(CH₂)₂)-2,8-diazaspiro[4.5]dec-8-yl | MS: 499 |
| 13 | Cl | (Z)-4-(HOCH₂CH=CH)-pipe | MS: 456 |
| 14 | Cl | (4R,5S)-4,5-diOH-azep | MI: 446 |
| 15 | Cl | (H₂N(CH₂)₂)(HO₂C(CH₂)₂)N— | MS: 447 |
| 16 | Cl | 4-(cyano-CH₂)-pipe | MS: 439 |
| 17 | Cl | 4-((HO(CH₂)₂)(Me)NOCO)-pipe | MS: 517 |
| 18/f | Cl | 4-(2-oxo-pyrr)-pipe | MS: 483 |
| 19 | Cl | 4-(2-oxo-1,3-oxazolidin-3-yl)-pipe | MS: 485 |
| 20 | Cl | 4-EtHNOC-pipa | MS: 472 |
| 21 | Cl | (cyclohexen-4-yl)NH— | MS: 412 |
| 22 | Cl | 4-OH-4-(AcO(CH₂)₃)-pipe | MS: 516 |
| 223 | F | 4-(HO(CH₂)₂CO)-pipa | ME: 457 |
| 224 | F | 4-(HOCH₂CO)-hpipa | ME: 457 |
| 225 | F | 4-(HO(CH₂)₂)-hpipa | MS: 443 |
| 226 | F | 4-Ac-pipa | ME: 427 |
| 227 | F | 4-(4-Py)-pipa | ME: 462 |
| 228 | F | 4-pipe-pipe | ME: 467 |
| 229 | F | 4-(Me₂NSO₂)-pipa | ME: 492 |
| 230/f | F | 4-(HO₂CCH₂)-pipa | MS: 443 |

TABLE 19

| Ex | R¹ | R² | Data |
|---|---|---|---|
| 231 | F | 4-(HOCH₂CO)-pipa | ME: 443 |
| 232 | F | 5-oxo-hpipa | ME: 413 |
| 233 | F | 4-HO-pipe | ME: 400 |
| 234 | F | 4-(HOCH₂)-pipe | ME: 414 |
| 235 | F | 4-(HO(CH₂)₂)-pipe | MS: 428 |
| 236 | F | 4-(HO(CH₂)₂)-pipa | ME: 429 |
| 237 | F | 5-oxo-1,4-diazocan-1-yl | MS: 427 |
| 238 | F | 4-OH-4-(HOCH₂)-pipe | MS: 430 |
| 239 | F | 4-(HO₂CCH₂)-pipe | MS: 442 |
| 240 | F | 4-(HO(CH₂)₃)-pipe | MS: 442 |
| 241 | F | (4R,5S)-4,5-diOH-azep | MN: 428 |
| 242 | F | 4-(H₂NOCCH₂)-pipe | MS: 441 |
| 243 | F | 4-(MeHNOCCH₂)-pipe | MS: 455 |
| 244/f | F | 4-(H₂NOCCH₂)-pipa | MS: 442 |
| 245 | Cl | (S)-3-(HO₂CCH₂)-pipe | MS: 458 |
| 246/f | Cl | (S)-3-(EtO₂CCH₂)-pipe | |
| 247 | Cl | 4-(HO₂CCH₂)-pipe | MS: 458 |
| 248/f | Cl | 4-(EtO₂CCH₂)-pipe | |
| 249 | Cl | HOCH₂CH(OH)CH₂NH— | MS: 406 |
| 250 | Cl | Me₂CHCH₂NH— | MS: 388 |
| 251/f | Cl | mor | MS: 402 |
| 252/f | Cl | 1,1-dioxo-tmor | MS: 450 |
| 253 | Cl | 5-oxo-hpipa | MS: 429 |
| 254 | Cl | 4-HO-pipe | MS: 416 |
| 255 | Cl | 4-(HOCH₂)-pipe | MS: 430 |
| 256 | Cl | 4-(HO(CH₂)₂)-pipe | MS: 444 |
| 257 | Cl | 4-(HO(CH₂)₂)-pipa | MS: 445 |

TABLE 20

| Ex | R¹ | R² | Data |
|---|---|---|---|
| 258 | Cl | 4-(HO₂C(CH₂)₂)-pipe | MS: 472 |
| 259/f | Cl | 4-(EtO₂C(CH₂)₂)-pipe | MS: 500 |
| 260 | Cl | 4-(HO₂CCH₂)-hPy | MS: 456 |
| 261/f | Cl | 4-(EtO₂CCH₂)-hPy | MS: 484 |
| 262 | Cl | hpipa | MS: 415 |
| 263/f | Cl | 4-Boc-hpipa | MS: 515 |
| 264 | Cl | pipa | MS: 401 |
| 265/f | Cl | 4-Boc-pipa | MS: 501 |
| 266 | Cl | 4-(HOCH₂CO)-pipa | ME: 459 |
| 267 | Cl | 4-(HO(CH₂)₂CO)-pipa | ME: 473 |
| 268 | Cl | 4(HOCH₂CO)-hpipa | ME: 473 |
| 269 | Cl | 4-(H₂NCO(CH₂)₂)-pipa | ME: 472 |
| 270 | Cl | 4-(HO(CH₂)₂O(CH₂)₂)-pipa | ME: 489 |
| 271 | Cl | 4-((HOCH₂)₂CH)-pipe | ME: 474 |
| 272 | Cl | 4-(HO(CH₂)₃)-4-OH-pipe | ME: 474 |
| 273/f | Cl | 4-(ethoxycarbonylmethylene)-pipe | MS: 484 |
| 274 | Cl | 4-(3-iPr-1,2,4-oxadiazol-5-yl)-pipe | MS: 510 |
| 275 | Cl | 4-(2-PyS)-pipe | MS: 509 |
| 276/f | Cl | 3-F₃C-5,6-dihydro[1,2,4]triazolo[4,3-a]pyrazin-7(8H)-yl | MS: 507 |
| 277 | Cl | 4-OH-4-(HOCH₂)-pipe | MS: 446 |
| 278 | Cl | 1,4,6,7-tetrahydro-5H-imidazo[4,5-c]pyridin-5-yl | MS: 438 |
| 279 | Cl | (S)-3-(HO(CH₂)₂)-pipe | MS: 444 |
| 280 | Cl | 2,8-diazaspiro[4.5]dec-8-yl | MS: 455 |

TABLE 21

| Ex | R¹ | R² | Data |
|---|---|---|---|
| 281 | Cl | (S)-3-(H₂NOCCH₂)-pipe | MS: 457 |
| 282 | Cl | (S)-3-(MeHNOCCH₂)-pipe | MS: 471 |
| 283 | Cl | 4-(H₂NOC(CH₂)₂)-pipe | MS: 471 |
| 284 | Cl | (E)-4-(H₂NOCCH=CH)-pipe | MS: 469 |
| 285 | Cl | (Z)-4-(H₂NOCCH=CH)-pipe | MS: 469 |
| 286 | Cl | 2-(HOCH₂OC)-2,8-diazaspiro[4.5]dec-8-yl | MS: 513 |
| 287 | Cl | 4-(HO(CH₂)₃HN)-pipe | MS: 473 |
| 288 | Cl | 4-(HO₂C(CH₂)₂HN)-pipe | MS: 487 |
| 289 | Cl | (E)-4-(HO₂CCH=CH)-pipe | MS: 470 |
| 290 | Cl | 2-Ac-2,8-diazaspiro[4.5]dec-8-yl | MS: 497 |
| 291 | Cl | 4-(HO₂C(CH₂)₃)-pipe | MS: 486 |
| 292 | Cl | 4-(HO(CH₂)₄)-pipe | MS: 472 |
| 293 | Cl | (3R,4S)-3,4-diOH-pyrr | MS: 418 |
| 294 | Cl | (Z)-4-(HO₂CCH=CH)-pipe | MS: 470 |
| 295 | Cl | 4-(MeHNOC(CH₂)₂)-pipe | MS: 485 |
| 296 | Cl | 4-(H₂NOC(CH₂)₃)-pipe | MS: 485 |
| 297 | Cl | 4-(MeHNOC(CH₂)₃)-pipe | MS: 499 |
| 298 | Cl | (E)-4-(HOCH₂CH=CH)-pipe | MS: 456 |
| 299 | Cl | 4-(iPrHNOCCH₂)-pipa | MS: 500 |
| 300 | Cl | 4-(H₂NOCCH₂)-pipa | MS: 458 |
| 301 | Cl | 4-(MeHNOCCH₂)-pipa | MS: 472 |
| 302 | Cl | 4-(Me₂NOCCH₂)-pipa | MS: 486 |
| 303 | Cl | (R)-4-(3-OH-pyrr)-pipe | MS: 485 |
| 304 | Cl | (S)-4-(3-OH-pyrr)-pipe | MS: 485 |
| 305 | Cl | (S)-4-(2-H₂NOC-pyrr)-pipe | ME: 512 |

TABLE 22

| Ex | R¹ | R² | Data |
|---|---|---|---|
| 306 | Cl | (S)-4-(3-F-pyrr)-pipe | MS: 487 |
| 307 | Cl | (R)-4-(3-F-pyrr)-pipe | MS: 487 |
| 308/f | Cl | 5-oxo-1,4-diazocan-1-yl | MS: 443 |
| 309/f | Cl | 4-oxo-1,5-diazocan-1-yl | MS: 443 |
| 310/f | Cl | 5-oxo-6,6-diMe-hpipa | MS: 457 |
| 311/f | Cl | 3-oxo-pipa | MI: 415 |
| 312 | Cl | 4-HO₂C-pipe | MI: 444 |
| 313 | Cl | 4-(Me₂NOC)-pipe | MS: 471 |
| 314/f | Cl | 4-(H₂NOC)-pipe | MS: 443 |
| 315 | Cl | 3-oxo-2,8-diazaspiro[4.5]dec-8-yl | MS: 469 |
| 316/f | Cl | 4-(HO(CH₂)₂)-5-oxo-hpipa | MI: 473 |
| 317/f | Cl | 4-(MeHNOC)-pipe | MS: 457 |
| 318/f | Cl | 4-(HO(CH₂)₂HNOC)-pipe | MS: 487 |
| 319 | Cl | 4-((HO(CH₂)₂)(Me)NOC)-pipe | MS: 501 |
| 320/f | Cl | 4-Me-5-oxo-hpipa | MS: 443 |
| 321 | Cl | 2,4,6,7-tetrahydro-5H-pyrazolo[4,3-c]pyridin-5-yl | MS: 438 |
| 322/f | Cl | 4-(AcHNCH₂)-pipe | MS: 471 |
| 323 | Cl | 4-H₂N-pipe | MS: 415 |
| 324 | Cl | 7,8-dihydropyrido[4,3-d]pyrimidin-6(5H)-yl | MN: 448 |
| 325/f | Cl | 1,1-dioxido-1,2,5-thiadiazepan-5-yl | MI: 465 |
| 326 | Cl | 4-(H₂NOCCH₂)-pipe | MN: 455 |
| 327 | Cl | 4-Me₂N-pipe | MS: 443 |
| 328 | Cl | 4-(H₂NCH₂)-pipe | MS: 429 |
| 329 | Cl | (S)-3-OH-pyrr | MS: 402 |
| 330 | Cl | (R)-3-OH-pyrr | MS: 402 |

TABLE 23

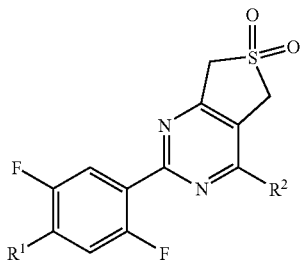

| Ex | R¹ | R² | Data |
|---|---|---|---|
| 331 | Cl | 4-(HOCH$_2$OCHNCH$_2$)-pipe | MS: 487 |
| 332 | Cl | 4-(HO(CH$_2$)$_3$HNOC)-pipe | MS: 501 |
| 333 | Cl | 4-(HOCH$_2$OCHN)-pipe | MS: 473 |
| 334 | Cl | 4-(H$_2$NOCCH$_2$)-hPy | MS: 455 |
| 335 | Cl | 4-(HO$_2$C(CH$_2$)$_3$HNOC)-pipe | MS: 529 |
| 336 | Cl | 4-(HO$_2$C(CH$_2$)$_2$HNOC)-pipe | MS: 515 |
| 337 | Cl | 4-OH-4-(HO$_2$CC≡C)-pipe | MS: 484 |
| 338 | Cl | 4-(HO(CH$_2$)$_2$HNOCO)-pipe | MS: 503 |
| 339 | Cl | 4-(MeHNOCCH$_2$)-pipe | MS: 471 |
| 340 | Cl | 4-(HO(CH$_2$)$_2$)-hPy | MS: 442 |
| 341 | Cl | (HO(CH$_2$)$_2$)NH— | MI: 376 |
| 342 | Cl | (3-Py(CH$_2$)$_2$)NH— | MI: 437 |
| 343 | Cl | trans-(4-OH-cHex)NH— | MI: 430 |
| 344 | Cl | (HO(CH$_2$)$_2$)(Me)N— | MI: 390 |
| 345 | Cl | (F(CH$_2$)$_2$)NH— | MI: 378 |
| 346 | Cl | 4-((HO(CH$_2$)$_2$)(Me)N)-pipe | MS: 473 |
| 347 | Cl | 4-(F(CH$_2$)NH)-pipe | MS: 461 |
| 348 | Cl | 4-(F$_3$CCH$_2$NH)-pipe | MS: 497 |
| 349 | Cl | 4-(pyrazol-1-yl)-pipe | MS: 466 |
| 350 | Cl | 4-(3-F$_3$C-pyrazol-1-yl)-pipe | MS: 534 |
| 351 | Cl | 4-(2H-triazol-2-yl)-pipe | MS: 467 |
| 352 | Cl | 4-pyrr-pipe | MS: 469 |
| 353 | Cl | 4-(thiazol-2-yl)-pipa | MS: 484 |
| 354 | Cl | cis-3,4-diOH-pipe | MS: 432 |
| 355 | Cl | (3S)-4-((3-OH-pyrr)OC)-pipe | MS: 513 |

TABLE 24

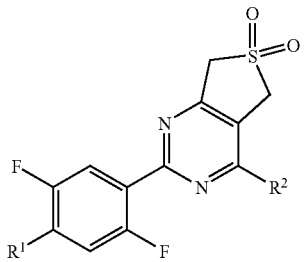

| Ex | R¹ | R² | Data |
|---|---|---|---|
| 356 | Cl | (3R)-4-((3-OH-pyrr)OC)-pipe | MS: 513 |
| 357 | Cl | 4-(pyrazol-3-yl)-pipe | MS: 466 |
| 358 | Cl | 4-OH-4-nBu-pipe | MS: 472 |
| 359 | Cl | (1S,4S)-5-Boc-2,5-diazabicyclo[2.2.1]heptan-1-yl | MS: 513 |
| 360 | Cl | (1S,4S)-5-Ac-2,5-diazabicyclo[2.2.1]heptan-1-yl | MS: 455 |
| 361 | Cl | (1S,4S)-2,5-diazabicyclo[2.2.1]heptan-1-yl | MS: 413 |
| 362/f | Cl | 4-EtO$_2$C-pipa | MS: 473 |
| 363 | Cl | 4-(EtO$_2$CCH$_2$)-pipe | MS: 486 |
| 364 | Cl | 4-(EtHNOCHNCH$_2$)-pipe | MS: 500 |
| 365 | Br | 4-(HOCH$_2$CO)-pipa | ME: 503, 505 |
| 366 | Br | 4-(HO(CH$_2$)$_2$CO)-pipa | ME: 517, 519 |
| 367 | Br | 4-(HOCH$_2$CO)-hpipa | ME: 517, 519 |
| 368 | Br | 5-oxo-hpipa | ME: 473, 475 |
| 369 | Br | 4-HO-pipe | ME: 460, 462 |
| 370 | Br | 4-(HOCH$_2$)-pipe | ME: 474, 476 |
| 371 | Br | 4-(HO(CH$_2$)$_2$)-pipe | ME: 488, 490 |

TABLE 24-continued

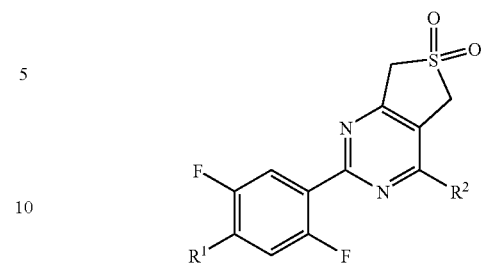

| Ex | R¹ | R² | Data |
|---|---|---|---|
| 372 | Br | 4-(HO(CH$_2$)$_2$)-pipa | ME: 489, 491 |
| 373/f | Br | 5-oxo-1,4-diazocan-1-yl | MI: 488 |
| 374 | MeS(O)— | 5-oxo-hpipa | ME: 457 |
| 375/f | MeS(O)$_2$— | 5-oxo-hpipa | ME: 473 |

TABLE 25

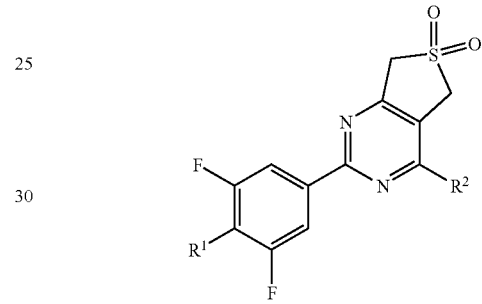

| Ex | R¹ | R² | Data |
|---|---|---|---|
| 376 | F | 4-HO-pipe | MS: 400 |
| 377/f | F | 4-(HOCH$_2$)-pipe | MS: 414 |
| 378/f | F | 5-oxo-hpipa | MS: 413 |
| 379 | F | 4-(HO(CH$_2$)$_2$)-pipa | MS: 429 |
| 380/f | F | 4-(HO(CH$_2$)$_2$)-pipa | MS: 420 |
| 381 | F | 4-(HO(CH$_2$)$_2$)-pipe | MS: 428 |
| 382/f | Cl | 4-HO-pipe | MS: 416 |
| 383/f | Cl | 4-(HOCH$_2$)-pipe | MS: 430 |
| 384 | Cl | 4-(HO(CH$_2$)$_2$)-pipe | MS: 444 |
| 385 | Cl | 5-oxo-hpipa | MS: 429 |
| 386 | Cl | 4-(HO(CH$_2$)$_2$)-pipa | ME: 445 |
| 387 | Cl | 4-(3-(HOCH$_2$)-pipe-)pipe | MF: 513 |
| 388 | Br | 4-HO-pipe | ME: 460 |
| 389 | Br | 4-(HOCH$_2$)-pipe | ME: 476 |
| 390 | Br | 4-(HO(CH$_2$)$_2$)-pipe | ME: 490 |
| 391 | Br | 5-oxo-hpipa | ME: 473 |
| 392 | Br | 4-(HO(CH$_2$)$_2$)-pipa | ME: 491 |

TABLE 26

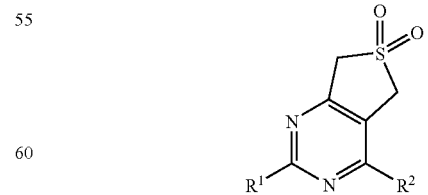

| Ex | R¹ | R² | Data |
|---|---|---|---|
| 393 | cPr | pipe | MS: 294 |
| 394 | cPr | mor | MS: 296 |
| 395 | cPr | azep | MS: 308 |

TABLE 26-continued

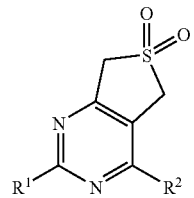

| Ex | R¹ | R² | Data |
|---|---|---|---|
| 396 | cPen | pipe | MS: 322 |
| 397 | cPen | mor | MS: 324 |
| 398 | cPen | azep | MS: 336 |
| 399 | cPen | 1,4-oxazepa-4-yl | MS: 338 |
| 400 | cPen | (4R,5S)-4,5-diOH-azep | MS: 368 |
| 401 | cPen | ((CH$_3$)$_2$CHCH$_2$)NH— | MS: 310 |
| 402 | cPen | trans-(4-OH-cHex)NH— | MS: 352 |
| 403 | cPen | ((CH$_3$)$_2$CHCH)(Me)N— | MS: 324 |
| 404 | cPen | cHex(Me)N— | MS: 350 |
| 405 | cPen | (HO(CH$_2$)$_2$)(Me)N— | MS: 312 |
| 406 | cPr | 4-(HO$_2$C(CH$_2$)$_3$)-pipe | MS: 380 |
| 407 | cPen | 4-(HO$_2$C(CH$_2$)$_3$)-pipe | MS: 408 |
| 408 | cPr | 4-(H$_2$NOC(CH$_2$)$_3$)-pipe | MS: 379 |
| 409 | cPen | 4-(H$_2$NOC(CH$_2$)$_3$)-pipe | MS: 407 |
| 410/f | cPen | 4-(HOCH$_2$)-pipe | MS: 352 |
| 411 | cPen | 5-oxo-hpipa | MS: 351 |
| 412 | cPen | 4-(3-iPr-1,2,4-oxadiazol-5-yl)-pipe | MS: 432 |
| 413 | cPen | 4-(HO$_2$CCH$_2$)-pipe | MS: 380 |
| 414 | cPen | 4-(H$_2$NOCCH$_2$)-pipe | MS: 379 |
| 415 | cPen | 5-oxo-1,4-diazocan-1-yl | MS: 365 |
| 416 | cPen | 4-(HO(CH$_2$)$_4$)-pipe | MS: 394 |
| 417 | cPen | 4-(HO(CH$_2$)$_3$)-pipe | MS: 380 |
| 418 | cPr | 4-(HO(CH$_2$)$_3$)-pipe | MS: 352 |
| 419 | cPr | 4-(EtO$_2$C(CH$_2$)$_3$)-pipe | MS: 408 |
| 420 | cPr | 4-(H$_2$NOC(CH$_2$)$_2$)-pipe | MS: 365 |

TABLE 27

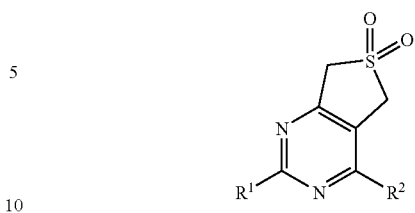

| Ex | R¹ | R² | Data |
|---|---|---|---|
| 421 | cPr | 1,4-oxazepan-4-yl | MS: 310 |
| 422 | cPr | 4-((HOCH$_2$)$_2$CH)-pipe | MS: 368 |
| 423 | cPr | 4-OH-4-(HOCH$_2$)-pipe | MS: 340 |
| 424 | cPr | 4-OH-4-(HO(CH$_2$)$_3$)-pipe | MS: 368 |
| 425 | cPr | hPy | MS: 292 |
| 426 | cPr | pyrr | MS: 280 |
| 427 | cPr | 4-(HO(CH$_2$)$_2$)-pipa | MS: 339 |
| 428 | cPr | ((CH$_3$)$_2$CHCH$_2$)NH— | MS: 282 |
| 429 | cPr | cHex(Me)N— | MS: 322 |
| 430 | cBu | 4-(EtO$_2$C(CH$_2$)$_3$)-pipe | MS: 422 |
| 431 | cBu | 4-(H$_2$NOC(CH$_2$)$_3$)-pipe | MS: 379 |
| 432 | cBu | 1,4-oxazepan-4-yl | MS: 324 |
| 433 | cPen | 4-(HO(CH$_2$)$_2$)-pipe | MS: 366 |
| 434 | cPen | 4-(EtO$_2$C(CH$_2$)$_2$)-pipe | MS: 422 |
| 435 | cPen | 4-(H$_2$NOC(CH$_2$)$_2$)-pipe | MS: 393 |
| 436 | cPen | 4-((HOCH$_2$)$_2$CH-)pipe | MS: 396 |
| 437 | cPen | 4-OH-4-(HOCH$_2$)-pipe | MS: 368 |
| 438 | cPen | 4-OH-4-(HO(CH$_2$)$_3$)-pipe | MS: 396 |
| 439 | cPr | (R)-3-Me-pipe | MS: 308 |
| 440 | cPr | 4-(HO(CH$_2$)$_4$)-pipe | MS: 366 |
| 441 | cPr | 4-(HO$_2$C(CH$_2$)$_2$)-pipe | MS: 366 |
| 442 | cBu | 4-(HO$_2$C(CH$_2$)$_3$)-pipe | MS: 394 |
| 443 | cBu | 4-(HO$_2$C(CH$_2$)$_2$)-pipe | MS: 380 |
| 444 | cPen | 4-(HO$_2$C(CH$_2$)$_2$)-pipe | MS: 394 |
| 445 | cBu | 4-(HO(CH$_2$)$_4$)-pipe | MS: 380 |

TABLE 27-continued

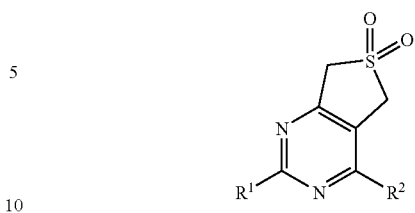

| Ex | R¹ | R² | Data |
|---|---|---|---|
| 446 | cBu | 4-(H$_2$NOC(CH$_2$)$_3$)-pipe | MS: 393 |
| 447 | cPr | 1-oxa-8-azaspiro[4.5]dec-8-yl | MS: 350 |
| 448 | cPr | (S)-3-Me-pipe | MS: 308 |

TABLE 28

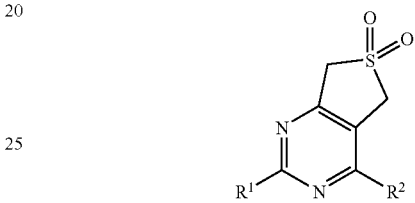

| Ex | R¹ | R² | Data |
|---|---|---|---|
| 449 | cPr | (S)-2-THF-CH$_2$NH— | MS: 310 |
| 450 | cPr | (R)-2-THF-CH$_2$NH— | MS: 310 |
| 451 | cBu | pipe | MS: 308 |
| 452 | cPr | 1,3-thiazolidin-3-yl | MS: 298 |
| 453 | cBu | 5-oxo-hpipa | MS: 337 |
| 454 | cBu | 4-(HOCH$_2$)-pipe | MS: 338 |
| 455 | cPr | 5-oxo-hpipa | MS: 323 |
| 456 | cPr | 4-(HOCH$_2$)-pipe | MS: 324 |
| 457 | cPr | 4-(HO(CH$_2$)$_2$)-pipe | MS: 338 |
| 458 | 2,5-diCl-3-the | 4-(HOCH$_2$)-pipe | MS: 434 |
| 459/f | 2-Cl-4-Py | 4-(HOCH$_2$)-pipe | MI: 395 |

TABLE 29

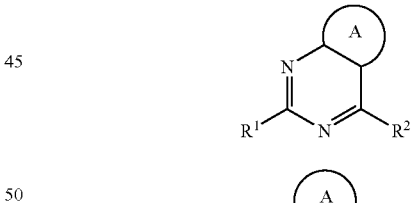

| Ex | R¹ | R² | Data |
|---|---|---|---|
| 7 | cPen | 4-(H$_2$NOCCH$_2$)-pipe | MS: 379 |
| 460 | 2,5-diF-4-Cl-Ph | mor | MS: 366 |

TABLE 29-continued

[Structure: pyrimidine core with R¹, R², and ring A substituents]

| Ex | R¹ | [R² group structure] | R² | Data |
|---|---|---|---|---|
| 461 | 2,5-diF-4-Cl-Ph | [3,4-dimethyl-2,5-dihydropyrrole] | Msmor | ME: 431 |
| 462 | 2,5-diF-4-Cl-Ph | [2,3-dimethyl-dihydrothiophene] | mor | MS: 370 |
| 463 | 2,5-diF-4-Cl-Ph | [2,5-dimethyl-dihydrothiophene] | mor | MS: 370 |

TABLE 30

[Structure: pyrimidine core with R¹, R², and ring A substituents]

| Ex | R¹ | [R² group structure] | R² | Data |
|---|---|---|---|---|
| 464 | 2,5-diF-4-Cl-Ph | [3,4-dimethyl-dihydrofuran] | mor | MS: 354 |
| 465 | 2,5-diF-4-Cl-Ph | [2,3-dimethyl-dihydrothiophene] | 4-HO-pipe | MS: 384 |
| 466 | 2,5-diF-4-Cl-Ph | [3,4-dimethyl-2,5-dihydropyrrole] | azep | MS: 365 |

TABLE 30-continued

[Structure: pyrimidine core with R¹, R², and ring A substituents]

| Ex | R¹ | [R² group structure] | R² | Data |
|---|---|---|---|---|
| 467 | 2,5-diF-4-Cl-Ph | [2,3-dimethyl-dihydrothiophene] | 4-(HO₂CCH₂)-pipe | MS: 426 |
| 468 | 2,5-diF-4-Cl-Ph | [2,3-dimethyl-dihydrothiophene-1,1-dioxide] | 4-(HO₂CCH₂)-pipe | MS: 458 |
| 469 | 2,5-diF-4-Cl-Ph | [2,3-dimethyl-dihydrothiophene] | 4-(HO₂CCH₂)-hPy | MS: 424 |

TABLE 31

[Structure: pyrimidine core with R¹, R², and ring A substituents]

| Ex | R¹ | [R² group structure] | R² | Data |
|---|---|---|---|---|
| 470/f | 2,5-diF-4-Cl-Ph | [2,3-dimethyl-dihydrothiophene] | 4-(EtO₂CCH₂)-hPy | MS: 452 |
| 471/f | 2,5-diF-4-Cl-Ph | [2,3-dimethyl-dihydrothiophene-1,1-dioxide] | 4-(HOCH₂)-pipe | MS: 430 |
| 472 | cPen | [2,3-dimethyl-dihydrothiophene] | 4-(HO₂CCH₂)-pipe | MS: 348 |
| 473/f | cPen | [2,3-dimethyl-dihydrothiophene-1,1-dioxide] | 4-(HOCH₂)-pipe | MS: 352 |

TABLE 31-continued

| Ex | R¹ | R² | | Data |
|---|---|---|---|---|
| 474 | cPen | [3,4-dimethyl-2,5-dihydrothiophene-1,1-dioxide-yl] | 5-oxo-hpipa | MS: 351 |
| 475 | cPen | [3,4-dimethyl-2,5-dihydrothiophene-1,1-dioxide-yl] | 3-iPr-1,2,4-oxadiazol-5-yl | MS: 432 |
| 476 | cPen | [3,4-dimethyl-2,5-dihydrothiophene-1,1-dioxide-yl] | 4-(HO₂CCH₂)-pipe | MS: 380 |

NMR data of compounds in some Examples are given in Tables 32 to 37 below. Symbols in Tables represent following meaning.

NMR: NMR data (δ(ppm)) of peaks in ¹H-NMR measured using tetramethylsilane as an internal standard and DMSO-d$_6$ as a solvent unless specifically noted).

TABLE 32

| Ex | Data |
|---|---|
| 1 | NMR: 0.90(3H, d), 1.14-1.26(1H, m), 1.44-1.58(1H, m), 1.60-1.84(3H, m), 2.74(1H, dd), 2.97-3.07(1H, m), 4.08-4.22(2H, m), 4.51(2H, s), 4.69(2H, s), 7.77(1H, dd), 7.97(1H, dd). |
| 2 | NMR: 1.10-1.28(4H, m), 1.46-1.59(2H, m), 1.59-1.72(1H, m), 1.76-1.88(2H, m), 2.05-2.16(2H, m), 2.17-2.25(2H, m), 2.95-3.04(2H, m), 3.07-3.25(4H, m), 4.51-4.75(2H, m), 7.94(1H, dd), 8.06(1H, dd). |
| 3 | NMR: 2.40-2.48(2H, m), 2.93-3.06(2H, m), 3.68-3.82(4H, m), 4.54(2H, s), 4.76(2H, s), 5.74(1H, s), 7.77(1H, dd), 8.00(1H, dd). |
| 6 | NMR: 2.90(3H, s), 3.23(4H, dd), 3.88(4H, dd), 4.10-4.23(2H, m), 4.33-4.45(2H, m), 6.25-7.50(1H, br), 7.77(1H, dd), 8.01(1H, dd). |
| 11 | NMR: 1.55-1.75(2H, m), 2.10-2.25(2H, m), 2.90-3.20(4H, m), 3.30-3.50(1H, m), 3.71(2H, t), 4.30-4.45(2H, m), 4.55(2H, s), 4.73(2H, s), 5.50-5.90(2H, br), 7.78(1H, dd), 8.00(1H, dd), 9.05-9.30(2H, br). |
| 14 | NMR: 1.70-1.84(2H, m), 1.88-2.02(2H, m), 3.54-3.82(6H, m), 4.48(2H, s), 4.74(2H, s), 7.72-7.80(1H, dd), 7.92-8.01(1H, dd). |
| 21 | NMR: 1.50-1.70(1H, m), 1.90-2.02(1H, m), 2.02-2.22(3H, m), 2.34-2.46(1H, m), 4.15-4.30(1H, m), 4.39(2H, s), 4.51(2H, s), 5.40-5.74(2H, m), 7.40-7.52(1H, d), 7.70-7.80(1H, dd), 7.88-7.98(1H, dd). |
| 31 | NMR: 1.26-1.34(1H, m), 1.42-1.59(4H, m), 1.77-1.82(2H, m), 2.07-2.14(2H, m), 2.28-2.32(2H, m), 2.97-3.25(6H, m), 4.45-4.48(2H, m), 7.83(1H, ddd), 8.11(1H, ddd). |
| 41 | NMR: 2.08(2H, quintet), 2.95(2H, t), 3.13(2H, t), 3.40-3.75(4H, m), 3.75-4.00(4H, m), 4.14(2H, s), 7.88(1H, dd), 8.04(1H, dd). |
| 54 | NMR: 1.55-1.70(2H, m), 1.90-2.20(4H, m), 2.60-2.75(1H, m), 2.90-3.03(2H, m), 3.05-3.20(2H, m), 3.25-3.40(2H, m), 4.40-4.60(2H, m), 7.93(2H, dd), 8.05(2H, dd). |
| 79 | NMR: 2.02-2.16(2H, m), 2.44-2.52(2H, m), 2.93-3.06(4H, m), 3.14-3.21(2H, m), 3.88-4.02(4H, m), 5.76(1H, s), 7.91(1H, dd), 8.06(1H, dd). |
| 149 | NMR: 2.21-2.33(2H, m), 2.98-3.06(2H, m), 3.83-3.92(2H, m), 4.15-4.22(2H, m), 4.26-4.35(2H, m), 4.43-4.50(2H, m), 5.58-5.65(1H, m), 7.65-7.77(1H, m), 8.00-8.13(1H, m). |
| 150 | NMR: 1.13-1.32(2H, m), 1.70-1.82(2H, m), 1.96-2.03(1H, m), 2.14-2.21(2H, m), 2.95-3.10(2H, m), 4.08-4.16(2H, m), 4.31-4.38(2H, m), 4.38-4.47(2H, m), 7.55-7.67(1H, m), 7.91-8.05(1H, m). |
| 152 | NMR: 1.03-1.30(4H, m), 1.45-1.63(3H, m), 1.66-1.80(2H, m), 2.20(2H, t), 2.91-3.05(2H, m), 4.07-4.14(2H, m), 4.30-4.38(2H, m), 4.38-4.50(2H, m), 7.50-7.68(1H, m), 7.92-8.05(1H, m). |
| 153 | NMR: 1.13-1.30(1H, m), 1.36-1.60(4H, m), 1.65-1.77(1H, m), 1.77-1.92(1H, m), 2.29(2H, t), 2.71-2.83(1H, m), 2.95-3.08(1H, m), 4.05-4.17(2H, m), 4.24-4.44(4H, m), 7.55-7.68(1H, m), 7.93-8.06(1H, m), 12.04(1H, s). |

TABLE 33

| Ex | Data |
|---|---|
| 154 | NMR: 1.24-1.40(1H, m), 1.44-1.62(1H, m), 1.66-1.79(1H, m), 1.79-1.88(1H, m), 1.89-2.04(1H, m), 2.15-2.32(2H, m), 2.93-3.06(1H, m), 3.06-3.17(1H, m), 4.15-4.22 (2H, m), 4.30-4.50(4H, m), 7.66-7.77(1H, m), 8.00-8.12(1H, m). |
| 166 | NMR: 1.18-1.30(2H, m), 1.74-1.80(2H, m), 1.96-2.08(1H, m), 2.18(2H, d), 3.02-3.11(2H, m), 4.15(2H, s), 4.37(2H, s), 4.43-4.49(2H, m), 7.77(1H, dd), 7.97(1H, dd). |
| 181 | NMR: 2.22-2.30(2H, m), 3.01(2H, s), 3.85(2H, t), 4.12-4.18(2H, m), 4.26-4.30(2H, m), 4.44-4.48(2H, m), 5.62(1H, s), 7.79(1H, dd), 8.01(1H, dd). |
| 183 | NMR: 1.26-1.40(1H, m), 1.46-1.62(1H, m), 1.68-2.02(3H, m), 2.17-2.30(2H, m), 2.94-3.15(2H, m), 4.16-4.20(2H, m), 4.30-4.50(4H, m), 7.80(1H, dd), 8.00(1H, dd). |
| 185 | NMR: 2.41(1H, dd), 2.57(1H, dd), 2.96(1H, dd), 3.15(1H, dt), 3.58(1H, dt), 3.75-5.00(9H, m), 7.75(1H, dd), 8.00(1H, dd). |
| 192 | NMR: 2.90-4.00(6H, m), 4.19(4H, s), 4.30-4.70(3H, m), 4.70-5.90(4H, m), 7.78(1H, dd), 8.04(1H, dd), 10.50-11.50(1H, br). |
| 196 | NMR: 1.13-1.30(2H, m), 1.70-1.81(2H, m), 1.93-2.07(1H, m), 2.17(2H, d), 2.96-3.09(2H, m), 4.08-4.15(2H, m), 4.30-4.37(2H, m), 4.38-4.48(2H, m), 7.82(1H, dd), 7.9(1H, dd), 12.09(1H, s). |
| 198 | NMR: 1.05-1.30(4H, m), 1.46-1.63(3H, m), 1.67-1.79(2H, m), 2.20(2H, t), 2.91-3.04(2H, m), 4.08-4.14(2H, m), 4.30-4.38(2H, m), 4.38-4.48(2H, m), 7.81(1H, dd), 7.91(1H, dd), 11.98(1H, s). |
| 231 | NMR: 3.40-3.65(4H, m), 3.65-3.85(4H, m), 4.13(2H, s), 4.55(2H, s), 4.76(2H, s), 7.67(1H, dt), 8.05(1H, ddd). |
| 232 | NMR: 2.60-2.75(2H, m), 3.25-3.38(2H, m), 3.70-3.90(4H, m), 4.55(2H, s), 4.71(2H, s), 7.50-7.80(2H, m), 8.05(1H, ddd). |
| 233 | NMR: 1.35-1.55(2H, m), 1.75-1.95(2H, m), 3.28-3.43(2H, m), 3.70-3.85(1H, m), 3.90-4.10(2H, m), 4.52(2H, s), 4.70(2H, s), 5.90-7.00(1H, br), 7.67(1H, dt), 8.02(1H, ddd). |
| 234 | NMR: 1.10-1.35(2H, m), 1.60-1.85(3H, m), 2.95-3.14(2H, m), 3.20-3.36(2H, m), 4.20-4.40(2H, m), 4.52(2H, s), 4.69(2H, s), 6.20-7.50(1H, br), 7.67(1H, dt), 8.02(1H, ddd). |
| 235 | NMR: 1.05-1.30(2H, m), 1.30-1.45(2H, m), 1.60-1.85(3H, m), 2.90-3.10(2H, m), 3.46(2H, t), 4.20-4.35(2H, m), 4.50(2H, s), 4.67(2H, s), 4.75-5.10(1H, br), 7.66(1H, dt), 8.01(1H, ddd). |
| 236 | NMR: 3.10-3.30(4H, m), 3.50-3.70(4H, m), 3.70-3.90(2H, m), 4.30-4.46(2H, m), 4.60(2H, s), 4.79(2H, s), 4.50-5.50(1H, br), 7.69(1H, dt), 8.10(1H, ddd), 10.80-11.20(1H, br). |
| 238 | NMR: 1.38-1.52(2H, m), 1.58-1.70(2H, m), 3.16-3.24(2H, m), 3.30-3.42(2H, m), 4.00-4.16(2H, m), 4.50(2H, s), 4.69(2H, s), 7.60-7.71(1H, m), 7.95-8.07(1H, m). |
| 241 | NMR: 1.70-1.84(2H, m), 1.88-2.02(2H, m), 3.54-3.82(6H, m), 4.49(2H, s), 4.74(2H, s), 7.61-7.72(1H, m), 7.95-8.06(1H, m). |

TABLE 34

| Ex | Data |
|---|---|
| 242 | NMR: 1.14-1.30(2H, m), 1.66-1.82(2H, m), 1.94-2.06(3H, m), 2.98-3.12(2H, m), 4.20-4.36(2H, m), 4.52(2H, s), 4.68(2H, s), 7.50-7.80(1H, m), 7.94-8.08(1H, m). |
| 251 | NMR: 3.40-3.50(4H, m), 3.60-3.75(4H, m), 4.54(2H, s), 4.74(2H, s), 7.76(1H, dd), 7.99(1H, dd). |
| 252 | NMR: 3.25-3.40(4H, m), 3.95-4.15(4H, m), 4.60(2H, s), 4.78(2H, s), 7.79(1H, dd), 8.04(1H, dd). |
| 253 | NMR: 2.60-2.70(2H, m), 3.25-3.40(2H, m), 3.70-3.95(4H, m), 4.55(2H, s), 4.71(2H, s), 7.00-7.60(1H, br), 7.60-7.72(1H, m), 7.78(1H, dd), 8.00(1H, dd). |
| 254 | NMR: 1.35-1.55(2H, m), 1.70-1.90(2H, m), 3.25-3.92(2H, m), 3.70-3.85(1H, m), 3.90-4.05(2H, m), 4.52(2H, s), 4.70(2H, s), 5.30-6.20(1H, br), 7.76(1H, dd), 7.97(1H, dd). |
| 255 | NMR: 1.10-1.30(2H, m), 1.60-1.81(3H, m), 2.90-3.10(2H, m), 3.28(2H, d), 3.20-3.34(2H, m), 4.52(2H, s), 4.69(2H, s), 6.30-7.40(1H, br), 7.76(1H, dd), 7.97(1H, dd). |
| 256 | NMR: 1.10-1.30(2H, m), 1.38(2H, q), 1.60-1.85(3H, m), 2.90-3.10(2H, m), 3.46(2H, t), 4.20-4.35(2H, m), 4.51(2H, s), 4.68(2H, s), 5.00-6.00(1H, br), 7.76(1H, dd), 7.97(1H, dd). |
| 257 | NMR: 3.00-3.30(4H, m), 3.45-3.75(4H, m), 3.75-3.90(2H, m), 4.30-4.50(2H, m), 4.60(2H, s), 4.80(2H, s), 5.40-5.80(1H, br), 7.79(1H, dd), 8.05(1H, dd). |
| 258 | NMR: 1.05-1.30(2H, m), 1.47(2H, q), 1.50-1.65(1H, m), 1.65-1.82(2H, m), 2.25(2H, t), 2.90-3.10(2H, m), 4.20-4.40(2H, m), 4.51(2H, s), 4.68(2H, s), 7.76(1H, dd), 7.97(1H, dd). |
| 262 | NMR: 2.00-2.20(2H, m), 3.00-3.22(2H, m), 3.22-3.35(2H, m), 3.74-3.84(2H, m), 3.95-4.08(2H, m), 4.55(2H, s), 4.60-5.60(3H, m), 7.78(1H, dd), 8.01(1H, dd), 9.20-9.50(2H, br). |
| 264 | NMR: 3.05-3.30(4H, m), 3.75-4.00(4H, m), 4.59(2H, s), 4.78(2H, s), 5.00-6.00(1H, br), 7.79(1H, dd), 8.04(1H, dd), 9.50-9.75(2H, br). |
| 266 | NMR: 3.40-3.65(4H, m), 3.65-3.85(4H, m), 4.13(2H, s), 4.56(2H, s), 4.76(2H, s), 7.78(1H, dd), 8.01(1H, dd). |
| 267 | NMR: 2.52(2H, t), 3.50-4.20(11H, m), 4.55(2H, s), 4.76(2H, s), 7.77(1H, dd), 8.01(1H, dd). |
| 268 | NMR: 1.70-1.94(2H, m), 3.35-3.50(2H, m), 3.52-3.65(1H, m), 3.65-3.80(3H, m), 3.80-3.87(1H, m), 3.87-3.95(1H, m), 4.00(1H, s), 4.08(1H, s), 4.51(1H, d), 4.73(2H, s), 5.00-6.50(1H, br), 7.70-7.84(1H, m), 7.99(1H, dd). |
| 269 | NMR: 2.70(2H, t), 3.00-3.22(2H, m), 3.26-3.38(2H, m), 3.44-3.54(2H, m), 3.54-3.70(2H, m), 4.30-4.50(2H, m), 4.61(2H, s), 4.80(2H, s), 4.80-5.10(1H, br), 7.00-7.20(1H, br), 7.54-7.74(1H, br), 7.79(1H, dd), 8.05(1H, dd), 11.30-11.70(1H, br). |
| 270 | NMR: 3.10-3.28(2H, m), 3.28-3.40(2H, m), 3.44-3.76(8H, m), 3.80-3.92(1H, m), 4.28-4.50(2H, m), 4.61(2H, s), 4.80(2H, s), 5.80-6.30(1H, br), 7.79(1H, dd), 8.05(1H, dd), 11.30-11.70(1H, br). |
| 271 | NMR: 1.25-1.44(3H, m), 1.65-1.85(3H, m), 2.97(2H, t), 3.32-3.55(4H, m), 4.25-4.42(2H, m), 4.51(2H, s), 4.70(2H, s), 4.80-5.50(1H, br), 7.76(1H, dd), 7.96(1H, dd). |

TABLE 34-continued

| Ex | Data |
|---|---|
| 272 | NMR: 1.30-1.62(8H, m), 3.30-3.45(4H, m), 3.95-4.20(2H, m), 4.51(2H, s), 4.70(2H, s), 4.72-5.10(1H, br), 7.76(1H, dd), 7.96(1H, dd). |

TABLE 35

| Ex | Data |
|---|---|
| 277 | NMR: 1.35-1.52(2H, m), 1.55-1.75(2H, m), 3.28-3.45(2H, m), 4.00-4.20(2H, m), 4.50(2H, s), 4.69(2H, s), 4.80-5.50(1H, br), 7.76(1H, dd), 7.97(1H, dd). |
| 279 | NMR: 1.15-1.60(4H, m), 1.60-1.90(3H, m), 2.81(1H, dd), 3.04(1H, dt), 3.42-3.55(2H, m), 4.21(2H, dd), 4.35-4.80(6H, m), 7.76(1H, dd), 7.98(1H, dd). |
| 281 | NMR: 1.20-1.35(1H, m), 1.45-1.60(1H, m), 1.65-2.15(4H, m), 2.86(1H, dd), 3.04(1H, dd), 3.80-4.40(3H, m), 4.49(1H, d), 4.54(1H, d), 4.68(2H, s), 6.86(1H, s), 7.34(1H, s), 7.76(1H, dd), 7.98(1H, dd). |
| 283 | NMR: 1.00-1.25(2H, m), 1.30-1.65(3H, m), 1.65-1.85(2H, m), 2.00-2.15(2H, m), 3.01(2H, t), 4.20-4.40(2H, m), 4.51(2H, s), 4.68(2H, s), 4.90-6.00(1H, br), 6.50-7.00(1H, br), 7.00-7.50(1H, br), 7.76(1H, dd), 7.97(1H, dd). |
| 284 | NMR: 1.25-1.50(2H, m), 1.70-1.88(2H, m), 2.20-2.40(1H, m), 3.11(2H, t), 4.20-4.40(2H, m), 4.52(2H, s), 4.70(2H, s), 4.80-5.30(1H, br), 5.87(1H, d), 6.59(1H, dd), 6.80-7.10(1H, br), 7.20-7.50(1H, br), 7.77(1H, dd), 7.98(1H, dd). |
| 285 | NMR: 1.25-1.45(2H, m), 1.65-1.78(2H, m), 3.08(2H, t), 3.65-3.80(1H, m), 4.20-4.40(2H, m), 4.51(2H, s), 4.69(2H, s), 4.60-5.30(1H, br), 5.70-5.85(2H, m), 6.80-7.20(1H, br), 7.25-7.50(1H, br), 7.76(1H, dd), 7.97(1H, dd). |
| 287 | NMR: 1.50-1.72(2H, m), 1.72-1.88(2H, m), 2.05-2.22(2H, m), 2.90-3.03(2H, m), 3.03-3.18(2H, m), 3.30-3.45(1H, m), 3.49(2H, t), 4.18-4.50(4H, m), 4.55(2H, s), 4.73(2H, s), 7.78(1H, dd), 7.99(1H, dd), 8.80-9.20(2H, br). |
| 288 | NMR: 1.50-1.75(2H, m), 2.09-2.22(2H, m), 2.76(2H, t), 3.00-3.22(4H, m), 3.28-3.50(1H, m), 4.28-4.44(2H, m), 4.55(2H, s), 4.74(2H, s), 7.78(1H, dd), 8.00(1H, dd), 9.10-9.35(2H, br). |
| 293 | NMR: 3.45-3.66(2H, m), 3.66-4.00(2H, m), 4.00-4.20(2H, m), 4.48(2H, s), 4.87(2H, s), 5.80-6.50(3H, br), 7.75(1H, dd), 7.97(1H, dd). |
| 296 | NMR: 1.10-1.30(4H, m), 1.40-1.64(3H, m), 1.65-1.83(2H, m), 2.03(2H, t), 3.01(2H, t), 4.20-4.40(2H, m), 4.51(2H, s), 4.68(2H, s), 5.15-5.90(1H, br), 6.50-6.85(1H, br), 7.00-7.45(1H, br), 7.76(1H, dd), 7.97(1H, dd). |
| 300 | NMR: 3.20-3.80(6H, m), 3.99(2H, s), 4.20-4.55(2H, m), 4.61(2H, s), 4.79(2H, s), 5.80-7.00(1H, br), 7.71(1H, s), 7.79(1H, dd), 8.05(1H, dd), 8.13(1H, s), 10.40-11.20(1H, br). |
| 311 | NMR: 3.32(2H, s), 3.80-3.90(2H, m), 4.25(2H, s), 4.55(2H, s), 4.83(2H, s), 7.74-7.82(1H, dd), 7.97-8.06(1H, dd), 8.19(1H, br). |
| 317 | NMR: 1.50-1.70(2H, m), 1.70-1.82(2H, m), 2.40-2.48(1H, m), 2.57(3H, d), 3.02-3.14(2H, m), 4.20-4.35(2H, m), 4.52(2H, s), 4.70(2H, s), 7.70-7.81(2H, m), 7.92-8.02(1H, dd). |
| 318 | NMR: 1.52-1.68(2H, m), 1.68-1.82(2H, m), 2.95-3.15(5H, m), 3.35-3.45(2H, m), 4.21-4.35(2H, m), 4.52(2H, s), 4.62-4.68(1H, t), 4.68-4.72(2H, s), 7.70-7.80(1H, dd), 7.80-7.88(1H, t), 7.92-8.02(1H, dd). |

TABLE 36

| Ex | Data |
|---|---|
| 319 | NMR: 1.50-1.80(4H, m), 2.81(2H, s), 2.90-3.20(5H, m), 3.30-3.35(1H, t), 3.40-3.50(2H, m), 3.50-3.60(1H, m), 4.20-4.40(2H, m), 4.52(2H, s), 4.71(2H, s), 7.70-7.81(1H, dd), 7.90-8.03(1H, dd). |
| 322 | NMR: 1.09-1.25(2H, m), 1.66-1.78(3H, m), 1.81(3H, s), 2.88-3.10(4H, m), 4.21-4.35(2H, m), 4.51(2H, s), 4.68(2H, s), 7.70-7.80(1H, dd), 7.80-7.91(1H, t), 7.92-8.01(1H, dd). |
| 323 | NMR: 1.46-1.68(2H, m), 1.92-2.10(2H, m), 3.06-3.22(2H, m), 3.26-3.44(1H, m), 4.23-4.37(2H, m), 4.55(2H, s), 4.72(2H, s), 7.72-7.83(1H, dd), 7.93-8.05(1H, dd), 8.25(2H, br). |
| 326 | NMR: 1.12-1.32(2H, m), 1.66-1.82(2H, m), 1.92-2.06(3H, m), 2.95-3.15(2H, m), 4.20-4.36(2H, m), 4.52(2H, s), 4.69(2H, s), 7.70-7.82(1H, dd), 7.90-8.02(1H, dd). |
| 330 | NMR: 1.83-2.02(2H, m), 3.54-3.90(4H, m), 4.32-4.39(1H, m), 4.39-4.47(1H, d), 4.49-4.56(1H, d), 4.89(2H, s), 7.70-7.80(1H, dd), 7.92-8.01(1H, dd). |
| 331 | NMR: 0.95-1.20(2H, m), 1.65-1.80(2H, m), 1.80-1.97(1H, m), 2.52-2.64(1H, m), 2.82-3.00(1H, m), 3.36(2H, t), 3.55-3.70(2H, m), 4.00-4.12(2H, m), 4.28-4.39(3H, m), 4.51(2H, s), 7.66(1H, t), 7.70-7.80(1H, dd), 7.90-8.00(1H, dd). |
| 333 | NMR: 1.40-1.63(2H, m), 1.70-1.87(2H, m), 3.10-3.26(2H, m), 3.90-4.00(1H, m), 4.05-4.15(1H, m), 4.15-4.30(2H, m), 4.53(2H, s), 4.95-4.934.69(4H, m), 7.65(1H, d), 7.73-7.81(1H, dd), 7.93-8.03(1H, dd). |
| 334 | NMR: 2.18-2.26(2H, m), 2.80-2.85(2H, m), 3.58-3.62(1H, m), 3.72-3.80(2H, m), 4.12-4.20(2H, m), 4.52(2H, s), 4.77(2H, s), 6.84(1H, br), 7.32(1H, br), 7.72-7.80(1H, dd), 7.95-8.03(1H, dd). |
| 341 | NMR: 2.08(1H, s), 3.45-3.65(4H, m), 4.40(2H, s), 4.53(2H, s), 7.70-7.80(1H, dd), 7.80-8.00(2H, m). |

TABLE 36-continued

| Ex | Data |
|---|---|
| 343 | NMR: 1.18-1.45(4H, m), 1.80-2.00(4H, m), 3.36-3.50(1H, m), 3.89-4.02(1H, m), 4.37(2H, s), 4.50(2H, s), 7.02(1H, br), 7.35-7.50(1H, d), 7.72-7.81(1H, dd), 7.90-8.00(1H, dd). |
| 348 | NMR: 1.66-1.84(2H, m), 2.16-2.30(2H, m), 3.00-3.16(2H, m), 3.42-3.60(1H, m), 4.02-4.18(2H, m), 4.32-4.46(2H, m), 4.56(2H, s), 4.74(2H, s), 6.86(1H, br), 7.72-7.84(1H, dd), 7.94-8.06(1H, dd). |
| 365 | NMR: 3.40-4.00(8H, m), 4.14(2H, s), 4.56(2H, s), 4.76(2H, s), 7.85(1H, dd), 7.96(1H, dd). |
| 366 | NMR: 2.52(2H, t), 3.45-4.00(10H, m), 4.55(2H, s), 4.76(2H, s), 7.86(1H, dd), 7.96 (1H, dd). |
| 367 | NMR: 1.70-1.94(2H, m), 3.35-3.52(2H, m), 3.52-3.65(1H, m), 3.65-3.80(3H, m), 3.80-3.87(1H, m), 3.87-3.95(1H, m), 4.00(1H, s), 4.08(1H, s), 4.51(2H, d), 4.73(2H, s), 4.70-5.30(1H, br), 7.80-7.90(1H, m), 7.94(1H, dd). |
| 368 | NMR: 2.58-2.70(2H, m), 3.20-3.36(2H, m), 3.65-3.90(4H, m), 4.00-4.50(1H, br), 4.55(2H, s), 4.70(2H, s), 7.86(2H, dd), 7.95(1H, dd). |
| 369 | NMR: 1.35-1.55(2H, m), 1.75-1.90(2H, m), 3.30-3.43(2H, m), 3.70-3.85(1H, m), 3.90-4.10(2H, m), 4.52(2H, s), 4.70(2H, s), 6.50-7.50(1H, br, 7.85(1H, dd), 7.93(1H, dd). |
| 370 | NMR: 1.10-1.30(2H, m), 1.60-1.82(3H, m), 2.90-3.12(2H, m), 3.20-3.34(2H, m), 4.20-4.40(2H, m), 4.51(2H, s), 4.68(2H, s), 6.10-7.50(1H, br), 7.85(1H, dd), 7.92(1H, dd). |

TABLE 37

| Ex | Data |
|---|---|
| 371 | NMR: 1.10-1.30(2H, m), 1.30-1.46(2H, m), 1.60-1.85(3H, m), 2.90-3.10(2H, m), 3.46(2H, t), 4.20-4.35(2H, m), 4.52(2H, s), 4.68(2H, s), 6.50-7.50(1H, br), 7.84(1H, dd), 7.92(1H, dd). |
| 372 | NMR: 3.10-3.30(4H, m), 3.50-3.70(4H, m), 3.75-3.90(2H, m), 4.30-4.46(2H, m), 4.61(2H, s), 4.80(2H, s), 5.50-6.50(1H, br), 7.87(1H, dd), 8.00(1H, dd), 11.00-11.40(1H, br). |
| 399 | NMR: 1.50-2.10(12H, m), 3.22(1H, quintet), 3.65(2H, t), 3.76(2H, t), 3.80-4.00(2H, m), 4.59(2H, s), 4.77(2H, s). |
| 407 | NMR: 1.05-1.30(4H, m), 1.40-1.90(11H, m), 1.90-2.10(2H, m), 2.20(2H, t), 3.00-3.26(3H, m), 3.50-4.50(3H, m), 4.59(2H, s), 4.71(2H, s). |
| 421 | NMR: 1.04-1.22(4H, m), 1.80-1.90(2H, m), 2.10-2.21(1H, m), 3.60-3.68(2H, m), 3.70-3.76(2H, m), 3.78-3.90(4H, m), 4.59(2H, s), 4.75(2H, s). |
| 422 | NMR: 1.00-1.20(6H, m), 1.25-1.40(3H, m), 1.70-1.85(4H, m), 2.05-2.15(1H, m), 2.90-3.10(2H, m), 3.32-3.52(4H, m), 4.25-4.40(1H, m), 4.56(2H, s), 4.68(2H, s). |
| 432 | NMR: 1.80-2.10(4H, m), 2.20-2.45(4H, m), 3.62-3.72(3H, m), 3.76-3.84(2H, m), 3.90-4.02(4H, m), 4.61(2H, s), 4.79(2H, s). |
| 436 | NMR: 1.25-1.45(3H, m), 1.55-1.90(9H, m), 1.95-2.10(2H, m), 3.00-3.17(2H, m), 3.18-3.30(1H, m), 3.30-3.50(4H, m), 4.30-4.80(4H, m), 4.62(2H, s), 4.73(2H, s). |
| 437 | NMR: 1.40-1.56(2H, m), 1.56-1.90(9H, m), 1.90-2.08(2H, m), 3.14-3.26(3H, m), 3.32-3.50(2H, m), 3.90-4.55(3H, m), 4.59(2H, s), 4.73(2H, s). |
| 442 | NMR: 1.10-1.30(4H, m), 2.45-1.70(4H, m), 1.75-1.95(4H, m), 1.95-2.10(1H, m), 2.15-2.40(6H, m), 3.06-3.22(2H, m), 3.58-3.72(1H, m), 4.43(1H, br), 4.59(2H, s), 4.72(2H, s). |
| 457 | NMR: 1.05-1.25(6H, m), 1.31-1.40(2H, m), 1.71-1.82(3H, m), 2.10-2.20(1H, m), 3.05-3.12(2H, t), 3.40-3.50(2H, t), 4.28-4.31(2H, m), 4.58(2H, s), 4.68(2H, s). |
| 469 | NMR: 2.26(2H, brs), 3.00(2H, brs), 3.27-3.40(4H, m), 3.81-3.83(2H, m), 4.25(2H, brs), 5.64(1H, s), 7.75(1H, dd), 7.98(1H, dd). |
| 471 | NMR: 1.02-1.04(2H, m)1.79-1.82(3H, m)3.16-3.41(6H, m), 3.69(2H, dd), 4.53(1H, dd), 4.72(2H, m), 7.79(1H, dd), 8-03(1H, dd). |

Chemical structures of other compounds of the present invention are given in Tables 38 and 39 below. These compounds are readily prepared using the above preparation methods, methods described in Examples, methods obvious to those skilled in the art, or modified methods thereof. Symbols in Tables represent the following meaning.

No: Compound Number

TABLE 38

| No | Structure |
|----|-----------|
| A1 | 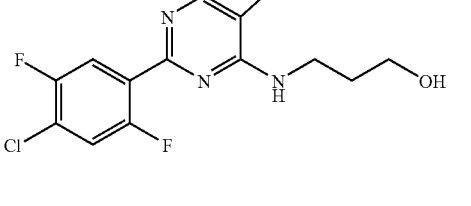 |
| A2 | 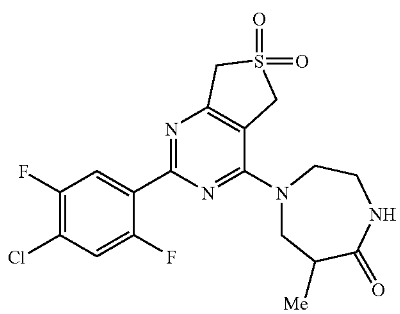 |
| A3 | 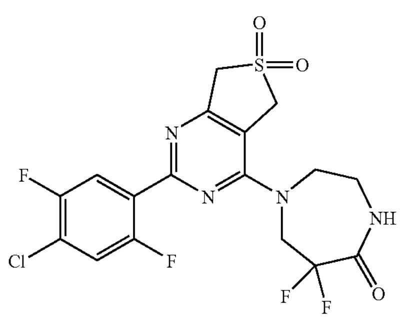 |
| A4 | 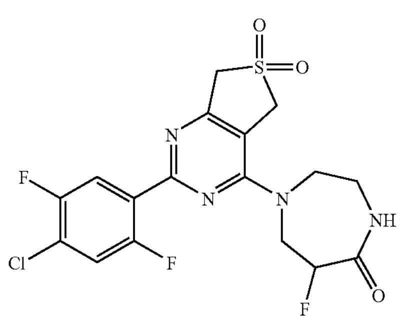 |

TABLE 38-continued

| No | Structure |
|----|-----------|
| A5 | 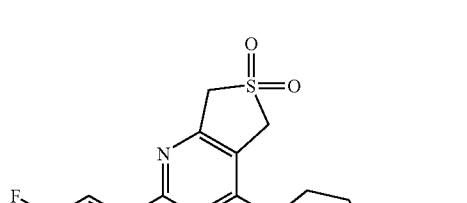 |
| A6 | 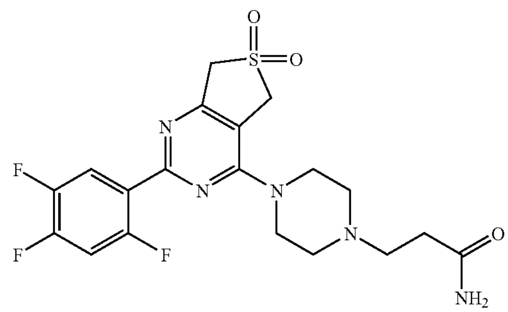 |
| A7 | 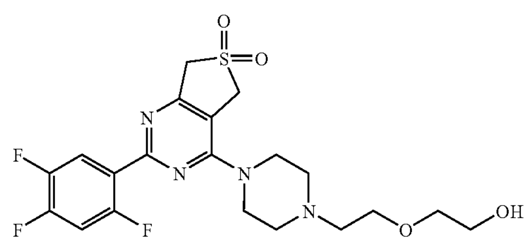 |
| A8 | 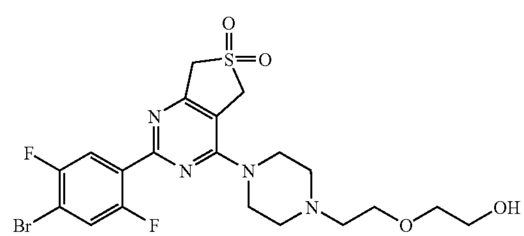 |
| A9 | 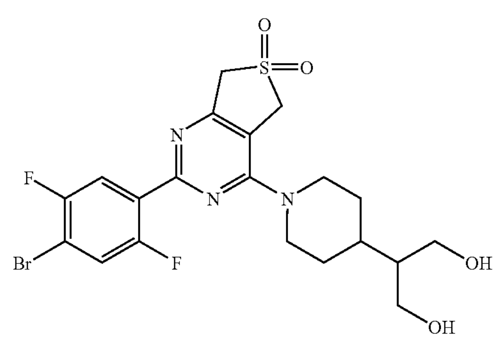 |

TABLE 38-continued
| No | Structure |
|---|---|
| A10 | 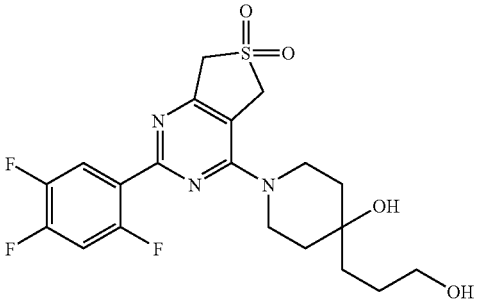 |
| A11 | 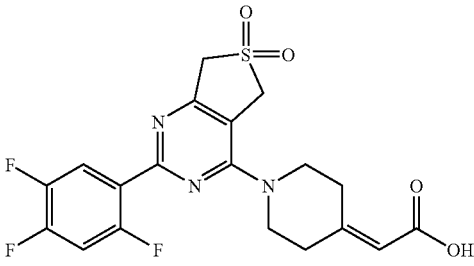 |
| A12 | 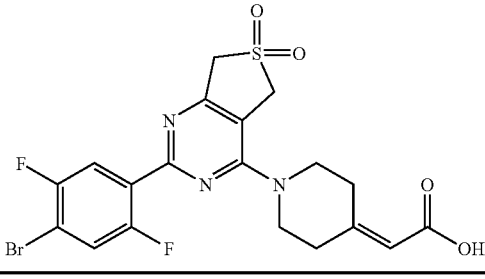 |
TABLE 39
| No | Structure |
|---|---|
| A13 | 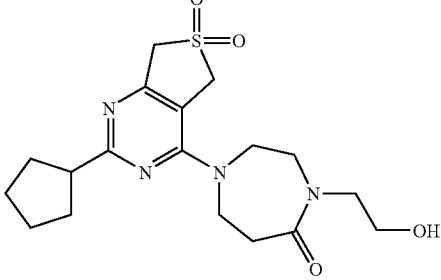 |
| A14 | 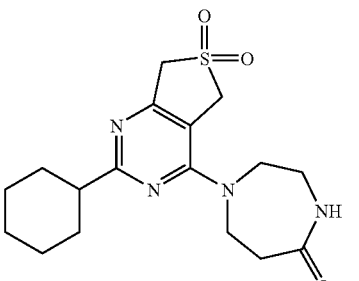 |
TABLE 39-continued
| No | Structure |
|---|---|
| A15 | 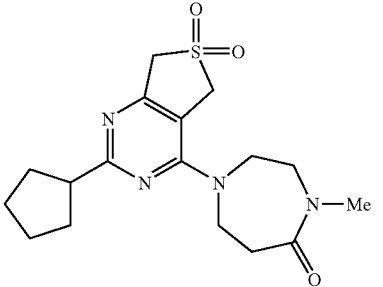 |
| A16 | 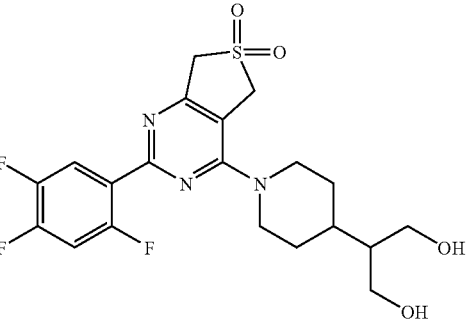 |
| A17 | 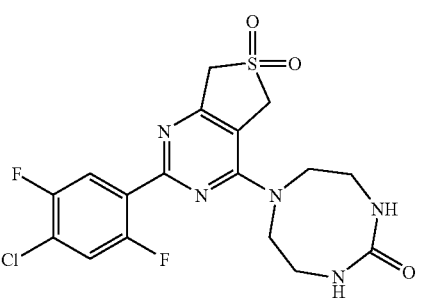 |
| A18 | 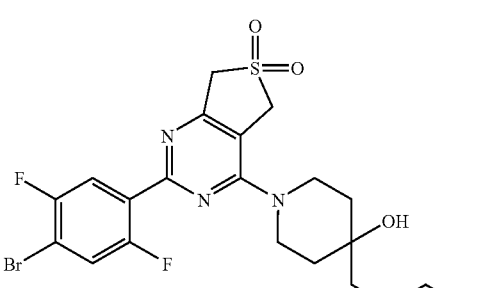 |
| A19 | 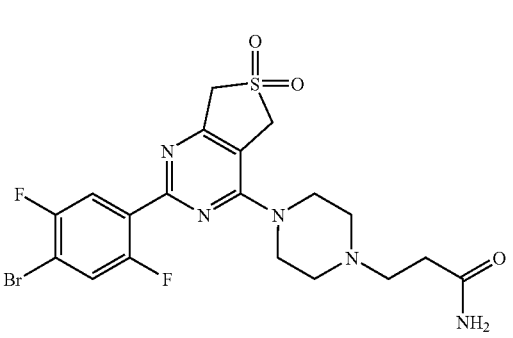 |

TABLE 39-continued

| No | Structure |
|---|---|
| A20 | (2-cyclopentyl-6,6-dioxido-5,7-dihydrothieno[3,4-d]pyrimidin-4-yl piperazinone) |
| A21 | (2-cyclohexyl-6,6-dioxido-5,7-dihydrothieno[3,4-d]pyrimidin-4-yl piperidinyl with propanediol) |
| A22 | (2-cyclopentyl-6,6-dioxido-5,7-dihydrothieno[3,4-d]pyrimidin-4-yl 1,1-dioxido-1,2,5-thiadiazepane) |

INDUSTRIAL APPLICABILITY

The compounds of the present invention exhibit excellent promoting activity on insulin secretion and preventive activity against hyperglycemia. Hence, the compounds of the present invention, based on these actions, are useful for treating and/or preventing insulin-dependent diabetes (type 1 diabetes), non-insulin-dependent diabetes (type 2 diabetes), insulin-resistant diseases, obesity, and the like.

What is claimed is:

1. A condensed pyrimidine compound represented by formula (I) or pharmaceutically acceptable salt thereof:

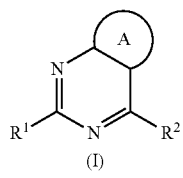

(I)

wherein
A represents a ring where at least one carbon atom within said ring is optionally substituted with one or more groups selected from the group consisting of lower alkyl, —O-(lower alkyl), halogen atom, carboxyl, —CO$_2$-(lower alkyl), and carbamoyl, where the sulfur atom within the ring is oxidized;
$R^1$ represents:
(1) phenyl substituted with at least three halogen atoms, which may have at least one additional substituent, or
(2) cyclopropyl, cyclobutyl, cyclopentyl, cyclohexyl, or cycloheptyl, each of which is optionally substituted; and
$R^2$ represents a group represented by formula (II) or an optionally substituted cyclic amino:

$$\begin{array}{c}\diagdown N \diagup R^{22} \\ | \\ R^{21}\end{array} \quad \text{(II)}$$

wherein $R^{21}$ and $R^{22}$ may be identical or different and each represents —H, lower alkyl, lower alkenyl, lower alkynyl, cycloalkyl, phenyl, heteroaryl, non-aromatic heterocyclyl, or —O-(lower alkyl), each of which is optionally substituted.

2. The compound according to claim 1, wherein $R^1$ is phenyl substituted with at least three halogen atoms.

3. The compound according to claim 2, wherein $R^2$ is optionally substituted cyclic amino.

4. The compound according to claim 3, wherein $R^2$ is optionally substituted piperazinyl or optionally substituted piperidinyl.

5. The compound according to claim 1, wherein $R^1$ is cyclopropyl, cyclobutyl, cyclopentyl, cyclohexyl, or cycloheptyl, each of which is optionally substituted.

6. The compound according to claim 5, wherein $R^1$ is cyclobutyl or cyclopentyl, each of which is optionally substituted.

7. The compound according to claim 6, wherein $R^2$ is optionally substituted cyclic amino.

8. The compound according to claim 7, wherein $R^2$ is optionally substituted piperazinyl or optionally substituted piperidinyl.

9. A condensed pyrimidine compound, or pharmaceutically acceptable salt thereof, selected from the group consisting of
3-{4-[2-(4-chloro-2,5-difluorophenyl)-6,6-dioxido-5,7-dihydrothieno[3,4-d]pyrimidin-4-yl]piperazin-1-yl}propanamide,
1-[2-(4-chloro-2,5-difluorophenyl)-6,6-dioxido-5,7-dihydrothieno[3,4-d]pyrimidin-4-yl]-4-(3-hydroxypropyl)piperidin-4-ol,
N-({1-[2-(4-chloro-2,5-difluorophenyl)-6,6-dioxido-5,7-dihydrothieno[3,4-d]pyrimidin-4-yl)piperidin-4-yl]methyl}-2-hydroxyacetamide,
3-{1-[2-(4-chloro-2,5-difluorophenyl)-6,6-dioxido-5,7-dihydrothieno[3,4-d]pyrimidin-4-yl]piperidin-4-yl}propanamide, 3-({1-[2-(4-chloro-2,5-difluorophenyl)-6,6-dioxido-5,7-dihydrothieno[3,4-d]pyrimidin-4-yl]piperidin-4-yl}amino)propan-1-ol, 3-({1-[2-(4-chloro-2,5-difluorophenyl)-6,6-dioxido-5,7-dihydrothieno[3,4-d]pyrimidin-4-yl]piperidin-4-yl}amino)propionic acid, 4-[1-(2-cyclopentyl-6,6-dioxido-5,7-dihydrothieno[3,4-d]pyrimidin-4-yl)piperidin-4-yl]butyric acid, 4-[1-(2-cyclobutyl-6,6-dioxido-5,7-dihydrothieno[3,4-d]pyrimidin-4-yl)piperidin-4-yl]butyric acid, and 4-{1-[2-(4-chloro-2,5-difluorophenyl)-6,6-dioxido-5,7-dihydrothieno[3,4-d]pyrimidin-4-yl]piperidin-4-yl}butyric acid.

10. A pharmaceutical composition comprising the compound according to claim 1 and one or more additives selected from the group consisting of a carrier, an inert diluent, a lubricant, a disintegrating agent, a stabilizer, a solubilizing agent, an adjuvant, a sweetener, a flavor, a fragrance, a preservative, an aqueous solvent, and a suspension medium.

11. A condensed pyrimidine compound represented by formula (I) or pharmaceutically acceptable salt thereof:

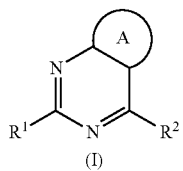

wherein
A represents a ring

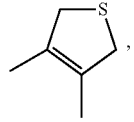

where at least one carbon atom within said ring is optionally substituted with one or more groups selected from the group consisting of lower alkyl, —O-(lower alkyl), halogen atom, carboxyl, —$CO_2$-(lower alkyl), and carbamoyl, where the sulfur atom within the ring is optionally oxidized;

$R^1$ is a phenyl substituted with at least three halogen atoms; and $R^2$ represents a group represented by formula (II) or an optionally substituted cyclic amino:

wherein $R^{21}$ and $R^{22}$ may be identical or different and each represents —H, lower alkyl, lower alkenyl, lower alkynyl, cycloalkyl, phenyl, heteroaryl, non-aromatic heterocyclyl, or —O-(lower alkyl), each of which is optionally substituted.

12. The compound according to claim 11, wherein $R^2$ is optionally substituted cyclic amino.

13. The compound according to claim 12, wherein $R^2$ is optionally substituted piperazinyl or optionally substituted piperidinyl.

* * * * *